(12) United States Patent
Travis et al.

(10) Patent No.: US 6,833,262 B1
(45) Date of Patent: Dec. 21, 2004

(54) POLYPEPTIDE HAVING AMIDOLYTIC ACTIVITY FOR A SERPIN

(75) Inventors: James Travis, Athens, GA (US); Jan S. Potempa, Athens, GA (US); Daniel C. Nelson, New York, NY (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 10/030,330

(22) PCT Filed: Apr. 20, 2000

(86) PCT No.: PCT/US00/10574

§ 371 (c)(1),
(2), (4) Date: Oct. 19, 2001

(87) PCT Pub. No.: WO00/63394

PCT Pub. Date: Oct. 26, 2000

Related U.S. Application Data

(60) Provisional application No. 60/130,436, filed on Apr. 21, 1999.

(51) Int. Cl.[7] .................. C12N 9/52; C12N 12/57; C12N 12/70; C12N 12/74; C12Q 1/37

(52) U.S. Cl. .................. 435/220; 435/23; 435/320.1; 536/23.2

(58) Field of Search .................. 435/220, 23, 320.1, 435/69.1, 252.3, 226; 536/23.2

(56) References Cited

U.S. PATENT DOCUMENTS 6,444,799 B1 * 9/2002 Ross .................. 536/23.1

FOREIGN PATENT DOCUMENTS

WO    WO 99 29870    4/1999

OTHER PUBLICATIONS

Bedi, G.S., et al., 1994, "Purification and characterization of a collagen–degrading protease from *Porphyromonas gingivalis*", The Journal of Biological Chemistry, vol. 269, pp. 599–606.*

Fletcher, H.M. et al., 1994, "Cloning and characterization of a new protease gene (prtH) from *Porphyromonas gingivalis*", Infection and Immunity, vol. 62, pp. 4297–4286.*

Altschul et al., "Gapped BLAST and PSI–BLAST: a new generation of protein database search programs," *Nucleic Acids Res.* Sep. 1, 1997;25(17):3389–402.

American Type Culture Collection, "ATCC No. 33277," organism: *Porphyromonas gingivalis*: designation: 2561 [online]; Manassas, VA [retrieved on Apr. 12, 2002] from the Internet. Retrieved from the Internet: <URL: http://www.atcc.org/SearchCatalogs/longview.cfm?view=ba, 6093556,33277&tex t=33277>; 2 pgs.

American Type Culture Collection, "ATCC No. 53978," organism: *Porphyromonas gingivalis*; designation: W50 [online]; Manassas, VA [retrieved on Apr. 15, 2002] from the Internet. Retrieved from the Internet:<http://www.atcc.org/SearchCatalogs/longview.cfm?view=ba,9154082,5 3978&text=53978>; 2 pgs.

(List continued on next page.)

*Primary Examiner*—Ponnathapura Achutamurthy
*Assistant Examiner*—William W. Moore
(74) *Attorney, Agent, or Firm*—Mueting, Raasch & Gebhardt, P.A.

(57) ABSTRACT

An isolated oral bacterial polypeptide having amidolytic activity for cleavage of denatured polypeptides and nondenatured serpin polypeptides and particularly a human $\alpha_1$-proteinase inhibitor polypeptide is provided. The mature polypeptide of the invention has a molecular weight of about 70 kD to about 80 kD. Also provided is an isolated nucleic acid sequence encoding the oral bacterial polypeptide of the invention, methods for identifying inhibitors of the polypeptide and compositions such as immunogenic compositions and inhibitor compositions.

32 Claims, 7 Drawing Sheets

OTHER PUBLICATIONS

Ausubel et al., eds., *Current Protocols in Molecular Biology*, vols. 1–4, John Wiley & Sons, Inc., New York, NY, 1994; title page, publisher's page and table of contents only (12 pages).

Banbula et al., "Propyl tripeptidyl peptidase from *Porphyromonas gingivalis*. A novel enzyme with possible pathological implications for the development of periodonitis," *J Biol Chem*. Apr. 2, 1999;274(14):9246–52.

Barrett et al., eds., *Handbook of Proteolytic Enzymes*, Academic Press, New York, NY, 1998; title page, publisher's page and table of contents only (14 pages).

Brosius et al., "Gene organization and primary structure of a ribosomal RNA operon from *Escherichia coli*," *J Mol Biol*. May 15, 1981;148(2):107–27.

Burdavari et al. eds., "Leupeptins," *The Merck Index*, 1996; Merck & Co., Inc., Whitehouse Station, NJ; item 5483, p. 932.

Carlsson et al., "Degradation of the human proteinase inhibitors alpha–1–antitrypsin and alpha–2–macroglobulin by *Bacteroides gingivalis*," *Infect Immun*. Feb. 1984;43(2):644–8.

Chen et al., "Purification and characterization of a 50–kDa cysteine proteinase (gingipain) from *Porphyromonas gingivalis*," *J Biol Chem*. Sep. 15, 1992; 267(26):18896–901.

Church et al., "Genomic sequencing," *Proc Natl Acad Sci U S A*. Apr. 1984; 81(7):1991–5.

Cox et al., "Detection of cathepsin B– and L–, elastase–, tryptase–, trypsin–, and dipeptidyl peptidase IV–like activities in crevicular fluid from gingivitis and periodontitis patients with peptidyl derivatives of 7–amino–4–trifluoromethyl coumarin," *J Periodontal Res*. Nov. 1989;24(6):353–61.

Cox et al., "Cathepsin B/L–, elastase–, tryptase–, trypsin– and dipeptidyl peptidase IV–like activities in gingival crevicular fluid. A comparison of levels before and after basic periodontal treatment of chronic periodontitis patients," *J Clin Periodontol*. May 1992;19(5):333–9.

Cutler et al., "Inhibition of C3 and IgG proteolysis enhances phagocytosis of *Porphyromonas gingivalis*," *J Immunol*. Dec. 15, 1993;151(12):7016–29.

Darany et al., "The relationship of gingival fluid leukocyte elastase activity to gingival fluid flow rate," *J Periodontol*. Sep. 1992;63(9):743–7.

Darveau et al., "Local chemokine paralysis, a novel pathogenic mechanism for *Porphyromonas gingivalis*," *Infect Immun*. Apr. 1998;66(4):1660–5.

Dashper et al., "Amino acid and peptide uptake by *Porphyromkonas gingivalis*," Abstract from International Association In Dental Research, Argentine division, XXX Annual Meeting. La Cumbre, Cordoba, Argentina. Oct. 23–25, 1997. *J Dent Res*. May 1998;77(5):1133 (abstract No. 36).

Davis, "Disc electrophoresis—II—method and application to human serum proteins," *Ann NY Acad Sci*. Dec. 1964;121(2):404–427.

Elliott et al., "Wild–type $\alpha_1$–antitrypsin is in the canonical inhibitory conformation," *J Mol Biol*. Jan. 23, 1998;275(3):419–25.

Fokkema et al., "A possible association of $\alpha_1$–antitrypsin deficiency with the periodontal condition in adults," *J Clin Periodontol*. Aug. 1998;25(8):617–23.

Genco et al., "A peptide domain on gingipain R which confers immunity against *Porphyromonas gingivalis* infection in mice," *Infect Immun*. Sep. 1998;66(9): 4108–14.

GenomeNet, "CLUSTALW: Multiple Sequence Alignment," [online], Bioinformatics Ceter, Institute for Chemical Research, Kyoto University, Kyoto, Japan; updated Dec. 03, 2000 [retrieved on Apr. 15, 2002]. Retrieved from the Internet: <URL: http://clustalw.genome.ad.jp/>; 2 pgs.

Grenier, "Degradation of host protease inhibitors and activation of plasminogen by proteolytic enzymes from *Porphyromonas gingivalis* and *Treponema denticola*," *Microbiology*. Apr. 1996;142(Pt 4):955–61.

Huynh et al., "Gingival crevicular fluid of patients with gingivitis or periodontal disease: evaluation of elastase–$\alpha_1$ proteinase inhibitor complex," *J Clin Periodontol*. Mar. 1992;19(3):187–92.

Imamura et al., "Dependence of vascular permeability enhancement on cysteine proteinases in vesicles of *Porphyromonas gingivalis*," *Infect Immun*. May 1995;63(5):1999–2003.

Institute for Genomic Research, "TIGR Databases," [online] Rockville, MD; [retrieved on Apr. 15, 2002]. Retrieved from the Internet: <URL:http://www.tigr.org/>; 2 pgs.

Jagels et al., "Proteolytic inactivation of the leukocyte C5a receptor by proteinases derived from *Porphyromonas gingivalis*," *Infect Immun*. Jun. 1996;64(6):1984–91.

Kadowaki et al., "Purification and characterization of a novel arginine–specific cysteine proteinase (argingipain) involved in the pathogenesis of periodontal disease from the culture supernatant of *Porphyromonas gingivalis*," *J Biol Chem*. Aug. 19, 1994;269(33):21371–8.

Karunakoran et al., "Isolation and characterization of a hemin–regulated gene, hemR, from *Porphyromonas gingivalis*," *J Bacteriol*. Mar. 1997;179(6):1898–908.

Kiyama et al., "Sequence analysis of the *Porphyromonas gingivalis* dipeptidyl peptidase IV gene," *Biochim Biophys Acta*. Mar. 4 1998;1396(1):39–46.

Kornman, "Controlled–release local delivery antimicrobials in periodontics: prospects for the future," *J Periodontol*. Aug. 1993;64(8–Suppl):782–91.

Kuramitsu, "Proteases of *Porphyromonas gingivalis*: what don't they do?" *Oral Microbiol Immunol*. Oct. 1998;13(5):263–70.

Madden et al., "Revised sequence of the *Porphyromonas gingivalis* prtT cysteine protease/hemagglutinin gene: homology with streptococcal pyrogenic exotoxin B/streptococcal proteinase," *Infect Immun*. Jan. 1995;63(1):238–47.

Madianos et al., "*Porphyromonas gingivalis* infection of oral epithelium inhibits neutrophil transepithelial migration," *Infection Immun*. Oct. 1997;65(10):3983–90.

Mast et al., "Kinetics and physiologic relevance of the inactivation of $\alpha_1$–proteinase inhibitor, $\alpha_1$–antichymotrypsin, and antithrombin III by matrix metalloproteinases–1 (tissue collagenase), –2 (72–kDa gelatinase/type IV collagenase), and –3 (stromelysin)," *J Biol Chem*. Aug. 25, 1991;266(24):15810–6.

Matsudaira, "Sequence from picomole quantities of proteins electroblotted onto polyvinylidene difluoride membranes," *J Biol Chem*. Jul. 25, 1987;262(21):10035–8.

Mikolajczyk–Pawlinska et al., "Modulation of interleukin–8 activity by gingipains from *Porphyromonas gingivalis*: implications for pathogenicity of periodontal disease," *FEBS Lett*. Dec. 4, 1998;440(3):282–6.

Miyasaki, "The neutrophil: mechanisms of controlling periodontal bacteria," *J Periodontol*. Dec. 1991;62(12):761–74.

Moore et al., "Bacteriology of severe periodontitis in young adult humans," *Infect Immun*. Dec. 1982;38(3):1137–48.

Nakayama et al., "Construction and characterization of arginine–specific cysteine proteinase (Arg–gingipain)–deficient mutants of *Porphyromonas gingivalis*. Evidence for significant contribution of Arg–gingipain to virulence," *J Biol Chem.* Oct. 6, 1995;270(40):23619–26.

National Center for Biotechnology Information, National Library of Medicine, National Institutes of Health, "BLAST 2 SEQUENCES," Bethesda, MD [retrieved on May 10, 2002]. Retrieved from the Internet: <URL: http://www.ncbi.nlm.nih.gov/blast/bl2seq/bl2.html>; 1 pg.

National Center for Biotechnology Information, National Library of Medicine, National Institutes of Health, GenBank Locus NM_000295, Accession No. NM_000295, "Homo sapiens serine (or cysteine) proteinase inhibitor, clade A (alpha–1 antiproteinase, antitrypsin), member 1 (SERPINA1), mRNA," [online]. Bethesda, MD [retrieved on May 10, 2002]. Retrieved from the Internet: <URL: http://www.ncbi.nlm.nih.gov/entrez/query.fcgi?cmd= Retrieve&db=nucleotide&li st_uids=4505792&dopt=GenBank>; 4 pgs.

National Center for Biotechnology Information, National Library of Medicine, National Institutes of Health, GenBank Locus PGU85038, Accession No. U85038, "*Porphyromonas gingivalis* arginine–specific cysteine proteinase RGP–2 (rgp2) gene, complete cds." [online]. Bethesda, MD [retrieved on May 10, 2002]. Retrieved from the Internet: <URL: http://www.ncbi.nlm.nih.gov/entrez/query. fcgi?cmd=Retrieve&db=nucleotide&li st_uids= 1814393&dopt=GenBank>; 3 pgs.

Nelson et al., "Inactivation of alpha1–proteinase inhibitor as a broad screen for detecting proteolytic activities in unknown samples," *Anal Biochem.* Jul. 1, 1998;260(2):230–6.

Nelson et al., "Purification and characterization of a novel cysteine proteinase (periodontain) from *Porphyromonas gingivalis*. Evidence for a role in the inactivation of human alpha1–proteinase inhibitor," *J Biol Chem.* Apr. 30, 1999;274(18):12245–51.

Otogoto et al., "Isolation and characterization of the *Porphyromonas gingivalis* prtT gene, coding for protease activity," *Infect Immun.* Jan. 1993;61(1):117–23.

Pike et al., "Lysine– and arginine–specific proteinases from *Porphyromonas gingivalis*. Isolation, characterization, and evidence for the existence of complexes with hemagglutinins," *J Biol Chem.* Jan. 7, 1994;269(1):406–11.

Potempa et al., "The inactivation of human plasma alpha 1–proteinase inhibitor by proteinases from *Staphylococcus aureus*," *J Biol Chem.* Oct. 25, 1986; 261(30):14330–4.

Potempa et al., "The serpin superfamily of proteinase inhibitors: structure, function, and regulation," *J Biol Chem.* Jun. 10, 1994;269(23):15957–60.

Potempa et al., "Host and *Porphyromonas gingivalis* proteinases in peridontitis: A biochemical model of infection and tissue destruction," *Perspectives in Drug Discovery and Design*, 1995;2(3):445–458.

Potempa et al., "*Porphyromonas gingivalis* proteinases in periodontitis, a review," *Acta Biochim Pol.* 1996;43(3):455–65.

Potempa et al., "Comparative properties of two cysteine proteinases (gingipains R), the products of two related but individual genes of *Porphyromonas gingivalis*," *J Biol Chem.* Aug. 21, 1998;273(34):21648–57.

Sambrook et al., *Molecular Cloning: A Laboratory Manual, Books 1–3*, Cold Spring Harbor Laboratory Press, Cold Spring Harbor, NY, 1989; title page, publisher's page and table of contents only (30 pgs).

Schägger et al., "Tricine–sodium dodecyl sulfate–polyacrylamide gel electrophoresis for the separation of proteins in the range from 1 to 100 kDa," *Anal Biochem.* Nov. 1, 1987;166(2):368–79.

Schenkein et al., "Increased opsonization of a prtH–defective mutant of *Porphyromonas gingivalis* W83 is caused by reduced degradation of complement–derived opsonins," *J Immunol.* May 15, 1995;154(10):5331–7.

Slots et al., "The occurrence of *Actinobacillus actinomycetemcomitans, Bacteroides gingivalis* and *Bacteroides intermedius* in destructive periodontal disease in adults," *J Clin Periodontol.* Jul. 1986;13(6):570–7.

Smalley et al., "The periodontopathogen *Porphyromonas gingivalis* binds iron protoporphyrin IX in the $\mu$–oxo dimeric form: an oxidative buffer and possible pathogenic mechanism," *Biochem J.* May 1, 1998;331 (Pt 3):681–5.

Smith et al., "Inhibition of crevicular fluid neutrophil elastase by $\alpha_1$–antitrypsin in periodontal health and disease," *Arch Oral Biol.* Apr. 1994; 39(4):301–6.

Socransky et al., "The bacterial etiology of destructive periodontal disease: current concepts," *J Periodontol.* Apr. 1992;63(4 Suppl):322–31.

Sugita et al., "Activation of transcription factors and IL–8 expression in neutrophils stimulated with lipopolysaccharide from *Porphyromonas gingivalis*," *Inflammation.* Jun. 1998;22(3):253–67.

Travis et al., "Human plasma proteinase inhibitors," *Annu Rev Biochem.* 1983; 52:655–709.

Travis et al., "The role of proteolytic enzymes in the development of pulmonary emphysema and periodontal disease," *Am J Respir Crit Care Med.* Dec. 1994; 150(6 Pt 2):S143–6.

Travis, James "Bacterial Proteinases in periodontal disease," Grant Abstract, Grant No. *5R01DE009761–10* [online]. National Institute of Dental & Craniofacial Research, National Institutes of Health, project dates Aug. 01, 1991 to Dec. 31, 2001 [retrieved on May 10, 2002]. Retrieved from the Internet: <URL:http://commons.cit.nih.gov/crisp3/ CRISP_LIB.getdoc?textkey=6342385& p_grant_num= 5R01DE009761–10&p_query=&ticket=943602&p_audit_session_id=5070993&p_keywords=>; 2 pgs.

Travis et al., "*Prophyromonas gingivalis* proteinases as virulence factors in the development of periodontitis," *J Periodontal Res.* Jan. 1997;32(1 Pt 2):120–5.

Uitto et al., "Oral fluid elastase as an indicator of periodontal health," *J Clin Periodontol.* Jan. 1996;23(1):30–7.

White et al., "Association of oral Bacteroides with gingivitis and adult periodontitis," *J Periodontal Res.* May 1981;16(3):259–65.

Wingrove et al., "Activation of complement components C3 and C5 by a cysteine proteinase (gingipain–1) from Porphyromonas (Bacteroides) gingivalis," *J Biol Chem.* Sep. 15, 1992;267(26):18902–7.

* cited by examiner

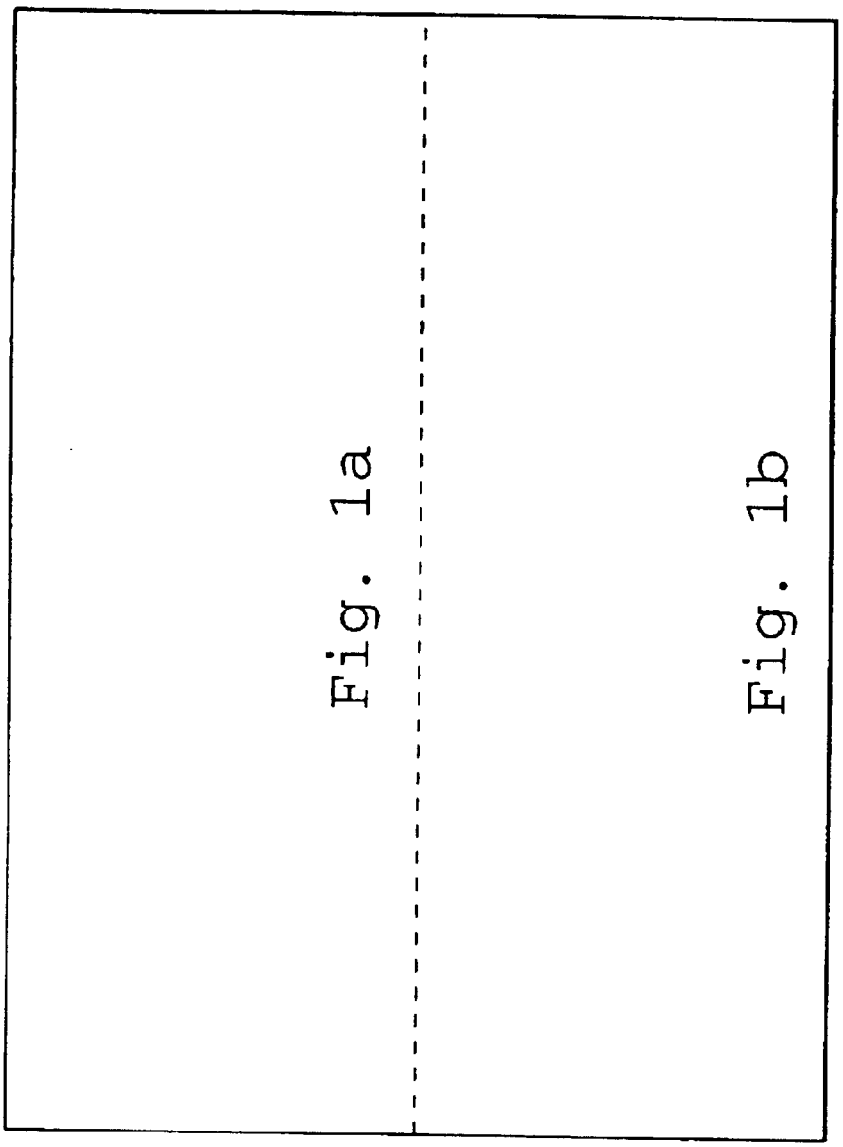

Fig. 1a

```
prtT         390  VP-GIVPDPTTLYGQHNMSDEA-LDESVKIKNYSTYAGDVKLAYRLTLPNGTETTNPA
Periodontain 399  AEAGTDALPIEALKDLEAEYKSESGLNVGYSIYNTGEEQSNLDLGYRLNKADGEVIEVKT prtT         448  VRNPIVWEDIIGESTGNITPCSQFAEGKNTISLLYRTDGMADWKELKHILMGLVNKIEV
Periodontain 459  SSNISWYG-YGEHPESFSLAPNQLSQGINTITLLYRRTGEQWEPMVRHAQGGYVNSIKV prtT         508  TMPAGDVAYSVAD---ARTVEKDGSLSHDLKAYSDCKESATVYNPGTEEFRSRVTFALRN
Periodontain 518  NTTDPNNVVTVDNNEGKLSHVPNSFVADLNSYEHSTLTVQFNSDSPDEIRTPVAFALST prtT         565  --TEGRLYFLGRHVELHPGDEDGEKVSLIITGLKARAGQYMLVCTGDMESLMEDASNIE
Periodontain 578  GATADDVISLGWVMAEVPGGSSN-YPVVWSKDVLTLSEGDYTLWYRFSIN--NQKDEWKK prtT         623  LASEVAEHTSTHSSLLVASNPQIDLLTVHRANPETLPTFSHTNEGGATFSGKTETVAIK
Periodontain 635  HGSVSVKTPTEYTHPLFEVGHNQTSTYTEDMAHNRVLPDFTEKNLG-LPENGEVVFRQ prtT         683  AFSEI-FFQAKEHMSLAQGETKVLSPETANSSLYTNAELFPDGTYIVREQG-FWDP
Periodontain 694  TQSSSGSLWAAQETWHLKQGETFVYKPVWEG------PIPDGSYRATLHAFVNGQQQ prtT         741  LDLFGDYYVRLRTLTDLSSSDIAGKDVSTIVNPNPAHDYVHVAIPPTYAGSTLRLFDLQ
Periodontain 745  LYLKGKRNYTVKLVNGTAVEAIE--SSEEIRVMPNPARDYVESAPCIPQERSILFDLS prtT         801  GRMQLSTKEESADMRLDVERLPKGTYIVVDMVGKHFIR-
Periodontain 803  GKHVMKNSLSAGHGRMDVSRLPNGAYILKDGYTTKGNIVH
```

Fig. 1b

MPSSVSWGILLAGLCCLVPVSLAEDPQGDAAQKTDTSHHDQDHP
TFNKITPNLAEFAFSLYRQLAHQSNSTNIFFSPVSIATAFAMLSLGTKADTHDEILEG
LNFNLTEIPEAQIHEGFQELLRTLNQPDSQLQLTTGNGLFLSEGLKLVDKFLEDVKKL
YHSEAFTVNFGDTEEAKKQINDYVEKGTQGKIVDLVKELDRDTVFALVNYIFFKGKWE
RPFEVKDTEEEDFHVDQVTTVKVPMMKRLGMFNIQHCKKLSSWVLLMKYLGNATAIFF
LPDEGKLQHLENELTHDIITKFLENEDRRSASLHLPKLSITGTYDLKSVLGQLGITKV
FSNGADLSGVTEEAPLKLSKAVHKAVLTIDEKGTEAA GAMFLEAIPMSIPPE VKFNKP
FVFLMIEQNTKSPLFMGKVVNPTQK

SEQ ID NO:3

Fig. 4

GAMFLEAIPMSIPPE

SEQ ID NO:4

```
ATGAAAAAAAGTTTTCTTTTAGCCATAGTAATGCTCTTTGGCATTGCCATGCAGGGACAT
TCTGCTCCGGTTACGAAAGAGCGAGCTTTGAGTCTGGCTCGGCTGGCTTTGCGACAGGTA
TCCTTGCGAATGGGACAAACAGCAGTATCTGACAAGATTTCCATCGATTACGTTTATCGG
CAAGGAGATGCTGAGAGGGGTATCACATCACAAGAGGAAGGCTCTCCTGCATATTTTTAT
GTAGCTAATCGTGGAAATAATGAGGGCTATGCTCTTGTAGCAGCAGATGACAGAATACCG
ACAATTTTAGCCTATTCACCCATTGGCCGTTTCGACATGGACAGTATGCCGGACAATCTT
CGCATGTGGCTACAAATTTACGATCAGGAAATAGGCCTGATACTTTCCGGAAAAGCTCAG
CTCAATGAAGAGATATTACGTACCGAGGGCGTACCGGCTGAAGTACATGCTCTGATGGAT
AACGGTCATTTTGCCAACGATCCCATGCGATGGAATCAAGGTTACCCATGGAACAATAAG
GAACCACTGCTTCCTAATGGCAATCATGCCTATACCGGCTGTGTTGCTACTGCTGCAGCA
CAAATCATGCGCTACCATAGCTGGCCGCTTCAAGGTGAAGGCTCTTTCGATTATCATGCA
GGTTCATTAGTTGGCAACTGGTCCGGCACATTTGGTGAAATGTACGACTGGATCAATATG
CCCGGAAATCCCGACCTTGATAATCTGACTCAATCTCAAGTGGATGCCTACGCCACACTG
ATGCGTGATGTGAGTGCATCTGTTTCGATGAGTTTTTATGAAAATGGAAGTGGTACGTAC
AGCGTTTATGTAGTAGGAGCCTTGCGAAACAACTTTCGCTACAAGCGTTCACTGCAGCTA
CATGTACGCGCCTTATATACCTCACAGGAGTGGCACGATATGATCCGCGGGGAACTTGCC
TCCGGAAGGCCGGTCTATTATGCAGGGAATAACCAGAGCATAGGACATGCTTTCGTTTGC
GATGGTTATGCTTCGGATGGTACTTTCCATTTCAACTGGGGTTGGGGAGGTGTTTCCAAC
GGCTTCTACAAACTAACACTCCTCTCGCCGACTTCGTTGGGTATCGGAGGTGAGGGAATA
GGTTTTACCATTTATCAAGAGATCATCACCGGTATCGAACCGGCTAAGACTCCCGCTGAA
GCCGGTACAGATGCCTTGCCGATCTTGGCACTGAAAGACATAGAAGCCGAGTATAAAAGT
GAATCCGGATTGAACGTAGGGTATTCGATATATAATACAGGTGAAGAGCAATCAAATCTT
GACCTCGGATACAGATTGAACAAGGCTGACGGAGAAGTCATAGAGGTGAAAACTTCATCT
ATCAATATCTCTTGGTACGGATACGGAGAGCATCCCGAGAGTTTCTCATTGGCACCTAAT
CAGTTGTCACAAGGAATCAACACCATCACCCTACTTTATCGTCGCACAGGCACCGAACAG
TGGGAGCCGGTACGGCATGCACAGGGAGGATATGTCAATAGCATTAAAGTAAATACGACA
GACCCGAACAATGTCGTAGTCACGGTAGATAATAACGAAGGCAAGCTCAGTATCGTCCCC
AACAGCTTTGTCGCAGATCTGAATTCTTATGAACATAGTACGATTACAGTACAGTTCAAT
AGCGACAGCCCTGATGAGATCCGTACACCCGTAGCCTTTGCTCTATCTACAGGAGCTACT
GCGGACGATGTAATATCTTTGGGCTGGGTAATGGCTGAAGTTCCGGCGGTAGCAGCAAC
TATCCGGTGGTTTGGTCTAAAGACGTTCTCACTCTCTCGGAAGGCGACTATACATTGTGG
TATAGATTTTCCATCAACAACCAAAAGGATGAATGGAAAAGATCGGAAGCGTGTCAGTA
AAAACACCGACAGAGTATACGCACCCCTTATTCGAAGTGGGCCATAATCAAACTTCTACC
TATACGCTGGATATGGCACACAACAGAGTATTGCCCGACTTTACACTCAAAAATCTCGGA
TTGCCTTTCAATGGTGAGTTGGTTGTTGTTTTCCGCCAAACACAATCCTCATCGGGGTCT
TTATGGGCAGCTCAAGAAACAGTACATATCAAGCAAGGAGAAACTTTCGTATATAAACCT
GTTGTCGAAGGCCCTATACCTGATGGATCCTATCGTGCGACCCTCCATGCATTCGTAAAC
GGACAACAACAGTTGTACCTCAAGGGGAAAAGGAACTACACGGTGAAGATCGTCAATGGT
ACAGCGGTAGAAGCAATAGAATCGTCAGAAGAGATCAGAGTATTCCCTAATCCGGCACGC
GATTATGTGGAAATATCGGCACCTTGCATTCCCCAAGAAACATCTATCATTCTTTTCGAT
CTGTCAGGCAAGATTGTCATGAAGAATAGTTTATCAGCGGGGCATGGCAGAATGGATGTC
AGCCGACTTCCTAATGGGGCCTACATCCTTAAGGTGGATGGATATACGACGAAAATAAAT
ATAGTGCACTAA
```

SEQ ID NO:2

US 6,833,262 B1

POLYPEPTIDE HAVING AMIDOLYTIC ACTIVITY FOR A SERPIN

The present application is a national stage filing of International Patent Application No. PCT/US00/10574, filed on Apr. 20, 2000, which in turn claims priority to U.S. Provisional Application Ser. No. 60/130,436, filed Apr. 21, 1999, both of which are incorporated herein by reference.

STATEMENT OF GOVERNMENT RIGHTS

The present invention was made with support from the National Institutes of Health under Grant No. DE09761. The government may have certain rights in the invention.

BACKGROUND

The anaerobe *Porphyromonas gingivalis* (*P. gingivalis*) has been implicated as a major causative organism of adult onset periodontal disease. Enzymes from this organism have been found to degrade several proteins, including, for example, collagen, fibrinogen, immunoglobulins, complement proteins, and fibronectin Recent evidence has shown that three proteinases released from *P. gingivalis* may have a physiological role in modulating the human immune system in addition to their general ability to degrade proteins. These three proteinases are referred to as gingipains and include arginine-specific gingipain A (RgpA) and arginine-specific gingipain B (Rgp B), which are capable of specifically cleaving after arginine residues, and lysine-specific gingipain (Kgp) which is able to specifically cleave after lysine residues. Working in concert, these proteinases have been shown to produce bradykinin from high molecular weight kininogen, either directly or indirectly (kallikrein activation), resulting in the enhancement of vascular permeability (Imamura, et al., *Infect, Immun.*, 63(5):1999–2003 (1995)). This mechanism, which is used to provide nutritional components for the growth and proliferation of *P. gingivalis*, is presumed to be responsible for both the increased gingival crevicular fluid (GCF) and edema clinically noted in periodontal pockets of patients with advanced periodontitis (Darany et al., *J. Periodontol.*, 63:743–747 (1992)).

The interaction of *P. gingivalis* with a host's immune system response has been paradoxical, in that *P. gingivalis* has demonstrated both pro-inflammatory and anti-inflammatory responses. For example, *P. gingivalis* lipopolysaccharide has been shown to increase mRNA levels of interleukin-8 (IL-8) in neutrophils (Sugita et al., *Inflammation*, 2(3):253–267(1998)), and gingipains R have been shown to increase neutrophil chemotaxis by release of C5a from C5 of the complement system (Wingrove et al., *J. Biol. Chem.*, 7(26):18902–18907 (1992)). However, these proteinases are also capable of cleaving the C5a receptor from infiltrating neutrophils (Jagels et al., *Infect. Immun.*, 64(6):198–1991 (1996)), thereby effectively neutralizing localized chemotactic activity. Additionally, *P. gingivalis* has the ability to inhibit both IL-8 accumulation in gingival epithelial cells (Darveau et al., *Infect. Immun.*, 66(4) :1660–1665 (1998)), as well as transepithelial migration (Madianos et al., *Infect, Immun.*, 65(10):3983–3990 (1997)).

These apparent activity contradictions may potentially be explained by the compartmentalization of the oral cavity, wherein distal activation of chemotactic components and proximal paralysis of these factors creates a "leukocyte wall" between the periodontal plaque and gingival epithelium (Miyasaki, *J. Periodontol.*, 2:761–774 (1991)). Indeed, it has been reported that _soluble gingipains can stimulate IL-8 activity, whereas membrane bound gingipains, with a limited ability to diffuse beyond the plaque surface, completely degrade IL-8 (Mikolajczyk-Pawlinska et al., *FEBS Lett.*, 440:282–286 (1998)).

The recruitment of neutrophils to the "leukocyte wall" through both the increased leakage of blood vessels and a chemotactic gradient at first appear to be suicidal to *P. gingivalis*. However, such a scenario is not likely, as *P. gingivalis* is known to have evolved mechanisms to survive in the presence of neutrophils. For example, *P. gingivalis* proteinases have been shown to degrade C3 complement and immunoglobulins (Schenkein et al., *J. Immunol.*, 154:5331–5337 (1995)), thereby averting opsonization and subsequent detection by a host. Furthermore, gingipain R has been shown to have an inhibitory effect on the oxidative burst utilized by neutrophils to kill microorganisms (Kadowaki et al., *J. Biol. Chem.*, 269(33):21371–21378 (1994)). Similarly, the bacterial outer membrane of *P. gingivalis* may function as an antioxidant sink due to the incorporation of large amounts of heme (Smalley et al., *J. Biochem.*, 331:681–685 (1998)).

Activated neutrophils in the leukocyte wall typically undergo degranulation due to the inability to phagocytize foreign organisms, thereby expelling large quantities of the proteinases human neutrophil elasase (HNE) and cathepsin G. Although these proteinases may cause abnormal connective tissue destruction, the presence of human plasma proteinase inhibitors (serpins) typically minimize connective tissue destruction by complexing with endogenous proteinases. These complexes are ultimately absorbed by the liver for degradation. For example, high protein levels of the $\alpha_1$-proteinase inhibitor ($\alpha$1-PI) have been detected in GCF samples from patients diagnosed with severe periodontal disease (Huynh et al., *J. Clin. Periodontol.*, 19:187–192 (1992)). However, despite the presence of $\alpha$1-PI a high HNE activity is observed indicating that the $\alpha$1-PI must be present in either complexed, oxidized, or proteolytically inactivated forms (Uitto et al., *J. Clin. Periodontol.*, 2:30–37 (1996)). This observation is supported by evidence showing that less than 35% of available $\alpha$1-PI in the GCF is active as an inhibitor (Smith et al., *Archs. Oral Biol.*, 22(4):301–306 (1994)). Additionally, it has been shown that patients with $\alpha_1$-PI deficiencies have a significantly higher frequency of periodontal pocket depths $\geq 5$ mm, thereby being predisposed to manifestations of periodontal disease (Fokkems et al., *J. Clin. Periodontol.*, 25:617–623 (1998)). Thus, there is a need for further understanding the interaction of such serpins with other oral bacterial proteinases.

SUMMARY OF THE INVENTION

Described herein are the isolation, purification and characterization of a polypeptide, particularly an oral bacterial polypeptide that interacts with a serpin such as the human serpin $\alpha_1$-PI. This polypeptide is referred to as "periodontain," not only because of its function as a proteinase, but also because this polypeptide may function as a putative factor in the dysregulation of serpin function in the periodontal cavity of an animal. Additionally, the deduced amino acid sequence of periodontain, as determined by both partial peptide sequencing of the purified polypeptide and characterization of the *P. gingivalis* genome is provided.

Accordingly, the present invention provides an isolated oral bacterial polypeptide which has amidolytic activity for cleavage of a nondenatured human ($\alpha_1$-proteinase inhibitor at a reactive site loop region of the inhibitor. The isolated polypeptide demonstrates amidolytic activity in a solution containing about 1 nM to about 500 mM Tris, about 500 µM to about 100 mM cysteine maintained at a pH of about 7 to about 8. Preferably, the polypeptide is isolated from *Porphyromonas gingivalis* and is a cysteine proteinase.

The polypeptide of the invention preferably has a molecular weight of about 70 kD to about 80 kD as determined by gel filtration. The polypeptide of the invention will preferably cleave the reactive site loop region of the inhibitor represented by SEQ ID NO: 4 between glutamine and alanine and also between phenylalanine and leucine.

The present invention also provides an isolated polypeptide that is an oral bacterial cysteine proteinase and has amidolytic activity for cleavage of a nondenatured serpin at a reactive site loop region of the serpin. The isolated polypeptide is preferably isolated from *Porphyromonas gingivalis*. The isolated polypeptide of the invention further has the capability to cleave a target polypeptide nonspecifically.

The present invention further provides an isolated polypeptide that is isolated from *Porphyromonas gingivalis* and has amidolytic activity for cleavage of a nondenatured serpin at a reactive site loop region of the serpin.

The isolated polypeptide preferably contains an amino acid sequence having a percentage amino acid identity of greater than 37% to that of amino acid 148 to amino acid 843 of SEQ ID NO: 1. More preferably, the isolated polypeptide contains an amino acid sequence having a percentage amino acid identity of greater than 52% to that of amino acid 148 to amino acid 629 of SEQ ID NO: 1. In particularly preferred embodiments, the isolated polypeptide has an amino acid sequence represented by SEQ ID NO: 1, an active analog or an active fragment thereof, and more preferably, an amino acid sequence represented by amino acid 148 to amino acid 843 of SEQ ID NO: 1, an active analog or an active fragment thereof.

The present invention further provides an isolated nucleic acid encoding an oral bacterial polypeptide which has amidolytic activity for cleavage of a nondenatured human $\alpha_1$-proteinase inhibitor at a reactive site loop region of the inhibitor. Also provided is an isolated nucleic acid encoding a polypeptide which is an oral bacterial cysteine proteinase and has amidolytic activity for cleavage of a nondenatured serpin at a reactive site loop region of the serpin. The present invention further provides an isolated nucleic acid encoding a polypeptide which is isolated from *Porphyromonas gingivalis* and has amidolytic activity for cleavage of a nondenatured serpin at a reactive site loop region of the serpin.

The isolated nucleic acid fragment of the invention preferably has a nucleotide sequence represented by SEQ ID NO: 2. The isolated nucleic acid fragment of the invention further preferably encodes a polypeptide having an amino acid sequence with a percentage amino acid identity of greater than 37% when compared to amino acid 148 to amino acid 843 of SEQ ID NO: 1.

The present invention also provides an isolated nucleic acid fragment as described herein wherein the complement of the nucleic acid fragment hybridizes to SEQ ID NO: 2 under hybridization conditions of 0.5 M phosphate buffer, pH 7.2, 7% sodium dodecyl sulfate (SDS), 10 mM ethylenediaminetetra-acetate (EDTA), at 68° C., followed by three 20 minute washes in 2×SSC (1×SSC is 0.15 M NaCl, 0.015 M sodium citrate), 0.1% SDS, at 65° C., wherein at least about 15 nucleotides of the complement hybridize.

The present invention further provides a method for identifying an inhibitor of a polypeptide which has amidolytic activity for cleavage of a nondenatured serpin at a reactive site loop region of a serpin. The method includes isolating an agent that inhibits the amidolytic activity of the polypeptide by incubating the polypeptide with the agent under conditions that promote amidolytic activity of the polypeptide and determining if the amidolytic activity of the polypeptide is reduced relative to the amidolytic activity of the polypeptide in the absence of the agent. Preferably, the polypeptide is isolated form *Porphyromonas gingivalis*.

The invention also provides an immunogenic composition having a polypeptide which has amidolytic activity for cleavage of a nondenatured serpin at a reactive site loop region of a serpin and is capable of eliciting antibodies in an animal.

Also provided is a composition containing an inhibitor to a polypeptide that has amidolytic activity for cleavage of a nondenatured serpin at a reactive site loop region of a serpin isolated from an oral bacterium.

Definitions

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations, and the like.

"Proteinase," "peptidase," and "protease" all refer to enzymes that catalyze the hydrolysis of peptide bonds in a polypeptide. A "peptide bond" or "amide bond" is a covalent bond between the alpha-amino group of one amino acid and the alpha-carboxyl group of another amino acid.

As used herein, the term "isolated" means that a polypeptide is either removed from its natural environment or synthetically derived. Preferably, the polypeptide is purified, i.e., essentially free from any other polypeptides and associated cellular products or other impurities.

"Amidolytic activity" refers to the ability of a polypeptide to catalyze the hydrolysis of at least one peptide bond in another polypeptide. The term "cleavage" can also be used to refer to the hydrolysis of a peptide bond in a polypeptide.

"Periodontain" refers to a polypeptide having amidolytic activity with respect to a target polypeptide. Preferably, the polypeptide is a cysteine proteinase that is isolated from an oral bacteria, such as, *P. gingivalis*. A "target polypeptide," as used herein, includes any denatured polypeptide and/or a native polypeptide, i.e., nondenatured, that contains at least one exposed contiguous amino acid region, such as a random coil as determined for example, by x-ray crystallography, that is susceptible to cleavage, preferably by periodontain. The exposed amino acid region typically contains at least about 3 contiguous amino acids, and preferably at least about 10 contiguous amino acids. Periodontain target polypeptides include, for example, serpin polypeptides in general and mammalian serpin polypeptides specifically. A preferred target polypeptide of the invention is the human serpin, $\alpha_1$-proteinase inhibitor ($\alpha_1$-PI) (SEQ ID NO: 3). With respect to a serpin polypeptide, the exposed amino acid region, e.g., random coil, as used herein, is referred to as a "reactive site loop" region or "RSL." The RSL region of human $\alpha_1$-PI is about 15 contiguous amino acids (SEQ ID NO: 4).

An "active analog" or "active fragment" of a polypeptide of the invention is one that has amidolytic activity by hydrolysis of a peptide bond present in the target polypeptide as described herein. Active analogs and active fragments are described in greater detail herein.

"Nucleic acid fragment" as used herein refers to a linear polymeric form of nucleotides of any length, either ribonucleotides or deoxynucleotides, and includes both double- and single-stranded DNA and RNA. A nucleic acid fragment may include both coding and noncoding regions that can be obtained directly from a natural source (e.g., a microorganism), or can be prepared with the aid of recombinant or synthetic techniques. A nucleic acid molecule may be equivalent to this nucleic acid fragment or it can include this fragment in addition to one or more other nucleotides or polynucleotides. For example, the nucleic acid molecule of the invention can be a vector, such as an expression or cloning vector.

"Percentage amino acid identity" refers to a comparison of the amino acids of two polypeptides as described herein. Amino acid alignment may be determined, for example, using the sequence alignment program CLUSTAL W available at www.genome.ad.ip/SIT/CLUSTALW.html. and percent amino acid identity may be determined by BLAST 2 SEQUENCES at National Center for Biotechnology Information (NCBI) website: www.ncbi.nlm.nih.gov.

BRIEF DESCRIPTION OF THE DRAWINGS

FIG. 1. Sequence Alignment of Periodontain, PrtT, and Streptopain.

The aligned putative gene products of prtT (SEQ ID NO: 5) and periodontain (SEQ ID NO: 1), both deduced from P. gingivalis strain W83 genome, and streptopain (SEQ ID NO: 6), from S. pyogenes, were aligned according to multiple sequence alignment using the sequence alignment program CLUSTAL W and the percent amino acid identity was determined by BLAST 2 SEQUENCES at NCBI using the default matrix. The black box(es) indicate that the same amino acid is present in a compared sequence as indicated, and grey box(es) indicate that a similar amino acid, e.g., a conservative amino acid substitution, is present in a compared sequence as indicated. The putative catalytic cysteine and histidine residues of streptopain are marked (*). The underlined residues indicate the obtained N-terminal sequence of the light chain of periodontain. The double underlined residues indicate the sequence obtained from both N-terminal sequencing of the heavy chain and DNA sequencing of the 69 basepair PCR product Arrows indicate the putative cleavage sites necessary to form a mature periodontain heterodimer polypeptide from a nascent polypeptide.

Figure 2:
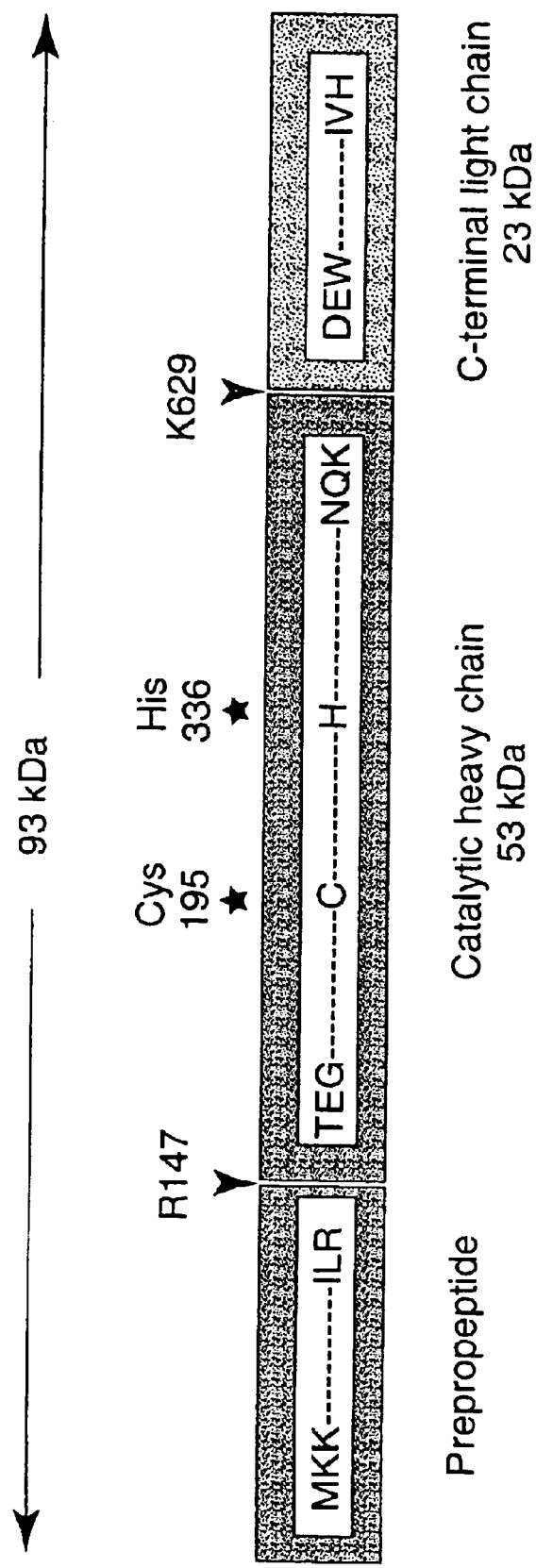

FIG. 2. Proposed Processing for the Maturation of Periodontain.

Structure of the periodontain polypeptide with proposed processing sites based on N-terminal sequencing of the purified heterodimer.

Figure 3:
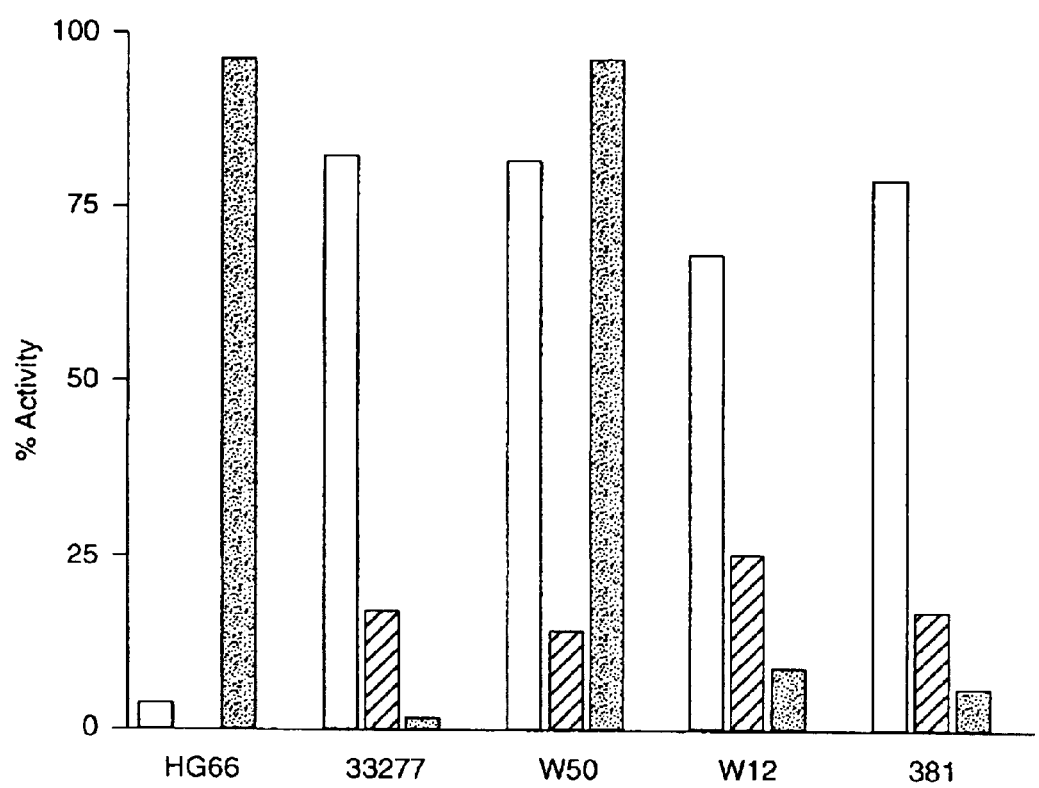

FIG. 3. Distribution of Period Atain Activity in Various P. gingivalis strains.

Periodontain activity from the indicated strains measured against human $\alpha_1$-PI using the assay as described in Material and Methods. Cell associated activities (clear bar), vesicle associated activities (hatched bar), and soluble activities (solid bar) were normalized to 100% for each strain.

FIG. 4. The Human $\alpha_1$-Proteinase Inhibitor Amino Acid Sequence.

The amino acid sequence of human $\alpha_1$-PI is shown. The RSL region of human $\alpha_1$-PI is identified.

FIG. 5. The Nucleic Acid Sequence of Periodontain.

The nucleic acid sequence for the full-length nascent polypeptide of the invention is shown.

FIG. 6. The RSL Region of Human $\alpha_1$-PI.

Detailed Description of Preferred Embodiments

Periodontal disease in an animal host, is typically characterized by inflammation of the periodontium manifested by recruitment of neutrophils which can degranulate, releasing powerfill proteinases responsible for destruction of connective tissues, and eventual loss of tooth attachment in the animal host. Although the presence of a host's innate proteinase inhibitors (i.e., serpins) may minimize tissue damage by endogenous proteinases, this is not clinically observed, and it has been speculated that proteolytic inactivation of a host's proteinase inhibitors may contribute to progression of the disease. A major pathogen associated with periodontal disease in an animal is the gram negative oral bacteria, Porphyromonas gingivalis. "Animal." as used herein, includes, for example, mammals, such as humans, sheep and dogs.

Described herein is a preferred polypeptide that has been isolated from the culture supernatants of Porphyromonas gingivalis. The polypeptide is capable of inactivating, for example, the nondenatured human serpin $\alpha_1$-proteinase inhibitor ($\alpha$1-PI), which is the primary endogenous regulator of human neutrophil elastase (HNE). A preferred polypeptide, referred to herein as periodontain, belongs to the cysteine proteinase family, and as a mature polypeptide, exists as a heterodimer. Periodontain (SEQ ID NO: 1) shares limited amino acid sequence identity to streptopain (SEQ ID NO: 6), a proteinase from Streptococcus pyogenes, and prtT (SEQ ID NO: 5), a putative proteinase from P. gingivalis (Table III and FIG. 1). Thus, a preferred polypeptide of the invention typically has a percentage amino acid identity of greater than 37% of the amino acid sequence including amino acid 148 to amino acid 843 of SEQ ID NO: 1. More preferably, the polypeptide of the invention has a percentage amino acid identity of greater than about 52%, even more preferably greater than about 70%, and most preferably greater than about 85% compared to the amino acid sequence of SEQ ID NO: 1.

Serpins, such as human $\alpha$1-PI, are single chain proteins containing a conserved domain structure of about 370 to about 390 residues, usually flanked by amino- or carboxyl-terminal extensions. Those present in plasma are also variably glycosylated, although the carbohydrate side chains are not required for activity. Inhibitory serpins interact with their target proteinase at a reactive site located within a loop structure 30 to 40 amino acids from the carboxyl terminus. This area is exposed on the surface of the protein and is susceptible to proteolysis by nontarget proteinases. See, for example, Potempa et al., J. Biol. Chem. 269:15957–1560 (1994).

The primary function of members of the serpin family is to neutralize overexpressed serine proteinase activity. This involves highly specific binding with a target enzyme by complex formation at a pseudo-reactive site peptide bond or "bait region" of the inhibitor. For example, the bait region in human $\alpha_1$-PI is the peptide bond between methionine (amino acid residue 358 of SEQ ID NO: 3) and serine (amino acid residue 359 of SEQ ID NO: 3). In the case of human $\alpha_1$-PI, the fidelity of this interaction is primarily dictated by the structure of the methionine residue which is usually in agreement with the cleavage specificity of the proteinase being inactivated. It has been shown that oxidation of human $\alpha_1$-PI converts the methionine amino acid residue to "Met-SO" (Travis et al., Annu. Rev. Biochem., 52:655–709 (1983)). Concomitant with this reaction is a dramatic loss of functional activity. It is now believed that, in vivo, this may be a mechanism to regulate elastase inhibitory activity at inflammatory sites. It is believed that the presence of periodontain in vivo, could result in elevated levels of HNE clinically detected in periodontal disease and may be a potential virulence factor for P. gingivalis.

Although it was recently demonstrated that *P. gingivalis* produces a proteinase that rapidly inactivates $\alpha_1$-PI, the proteinase was not isolated (Nelson et al., *Anal. Biochem.*, 260:230–236 (1998)) until now.

The present invention provides an isolated polypeptide, preferably an isolated proteinase, and more preferably a cysteine proteinase, that has amidolytic activity as evidenced by the hydrolysis of a peptide bond present in a target polypeptide. In general, the amidolytic activity of the polypeptide can be measured by assay of the cleavage of a target polypeptide in the presence of the polypeptide and a buffer (see, for example, Example 1). Preferably, the polypeptide is isolated from an oral bacteria. "Oral" as used herein, refers to biological material, such as bacteria, that can be found and isolated from the mouth of an animal.

Figure 1A:
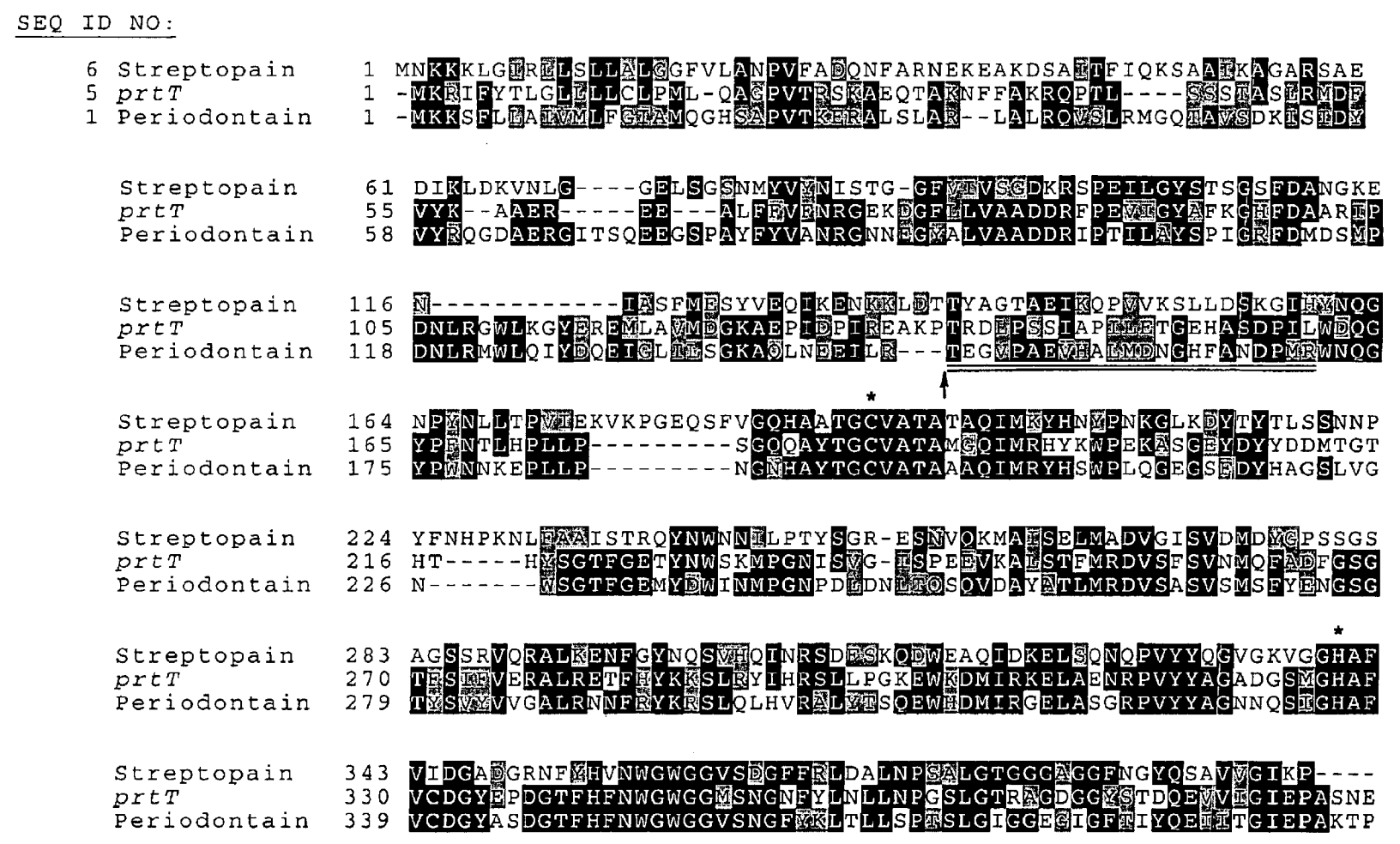

In its nascent form, the isolated polypeptide of the invention contains about 843 amino acid residues and has a molecular weight of about 93 kD (FIG. 1). "Nascent," as used herein, refers to a full-length unprocessed 93 kD polypeptide containing amino acid 1 to amino acid 843 of SEQ ID NO: 1 and as shown in FIG. 1. The 93 kD polypeptide is unprocessed in that it contains additional no acids not present in the mature polypeptide of the invention.

As shown in FIG. 2, proteolytic processing of the nascent 93 kD polypeptide at amino acid 147 (Arg) and amino acid 629 (Lys) yields a prepro-polypeptide (amino acids 1–147), a heavy chain polypeptide containing a catalytic region (amino acids 148–629), and a light chain polypeptide containing the C-terminal portion of the polypeptide corresponding to amino acid 630 to amino acid 843. As used herein, the "catalytic region" or "catalytic subunit" of the heavy chain polypeptide of periodontain (or any polypeptide described herein) is a region that is able to cleave, i.e., hydrolyze, a target polypeptide, particularly a nondenatured serpin. For example, in the RSL region of non-denatured human serpin $\alpha_1$-PI, periodontain will specifically cleave the peptide bond between glutamic acid and alanine residues (amino acids 354 and 355, respectively, of SEQ ID NO: 3). Typically, cleavage of this peptide bond is observed in vitro in a solution containing a Tris buffer in a concentration of about 1 millimolar (mM) to about 500 mM, about a 500 micromolar ($\mu$M) to about 100 mM cysteine at a pH of about 7 to about 8 and a temperature of about 18° C. to about 42° C. Preferably the solution contains about 50 mM Tris, about 20 mM cysteine maintained at a pH of about 7.4. Although cleavage of the peptide bond may occur at ambient temperature (typically about 25° C. to about 30° C.), preferably a temperature of about 37° C. is employed. Periodontain will also specifically cleave the peptide bond between phenylalanine and leucine residues (amino acids 352 and 353, respectively of SEQ ID NO: 3) under the solution conditions set forth above. Cleavage of this latter peptide bond occurs at about half the catalytic rate as cleavage of the peptide bond between the glutamic acid and alanine residues described above.

Without being bound by any specific theory, periodontain and other polypeptides of the invention are additionally characterized by the nonspecific proteolysis of a target polypeptide in that a specific amino acid residue residing in the polypeptide does not necessarily dictate the specificity of the proteinase. For example, periodontain will cleave any target polypeptide nonspecifically in a denaturing environment. A "denaturing environment," as used herein, includes in vitro environment conditions, for example, heat, strong reducing agents, such as dithiothreitol and $\beta$-mercaptoethanol, sodium dodecyl sulfate, or other chemical manipulation including carboxymethylate-maleylate treatment. A "denaturing environment" also includes in vivo denaturing environment conditions, such in vivo denaturing environment conditions may be provided by the catalytic action of other in vivo polypeptides, for example, gingipain A and gingipain B.

A "mature polypeptide" of the invention is a heterodimer and contains the heavy polypeptide chain, the light polypeptide chain and has proteolytic enzymatic activity. The polypeptide is mature in that it lacks the prepro region of the nascent polypeptide, e.g., amino acid 1 to amino acid 147 or SEQ ID NO: 1, and is not associated with a tRNA. The mature polypeptide has a predicted molecular weight of about 70 kD to about 80 kD, and preferably a molecular weight of about 75 kD to about 77 kD as determined by gel filtration. The heavy polypeptide chain typically has a molecular weight of about 50 kD to about 57 kD, and preferably a molecular weight of about 52 kD to about 55 kD as determined by gel filtration. The heavy chain preferably contains the catalytic site of the polypeptide. The mature polypeptide also contains the C-terminal light chain having a molecular weight of about 20 kD to about 25 kD, preferably a molecular weight of about 22 kD to about 24 kD. The C-terminal light chain appears to be devoid of enzymatic activity. Additionally, the mature polypeptide has an isoelectric focusing point (pI) of about 5.1 to about 5.5.

The in vivo activity of periodontain may have important physiological significance, as it may lead to the inactivation of many biologically active polypeptides and/or transformation of the activity of other biologically active polypeptides. In addition, hydrolysis of peptide bonds by periodontain in conjunction with general catabolic pathways should allow the complete re-utilization of amino acids by living organisms, including bacteria However, proteinases from bacterial pathogens, if released into the host environment, may interfere with the physiological functions of biologically active polypeptides and, therefore, contribute to the pathogenicity of infectious disease.

The external (i.e., cell surface) localization and uncontrolled activity of a bacterial proteinase, including periodontain, likely contributes significantly to run-away inflammation in the animal host and the pathological degradation of connective tissue during periodontitis. Periodontain, although unable to degrade proteins such as azocasein, casein, lysozyme, collagen, fibrin, plasminogen, and fibrinogen in nature, may be capable of degrading these proteins in vitro if present in a denaturing environment as described above. For example, when lysozyme is denatured, i.e., carboxymethylated-maleylated lysozyme, complete digestion of the reduced form of lysozyme by periodontain rapidly occurs. This characteristic indicates that periodontain will readily cleave denatured or easily accessible polypeptides, but is typically unable to cleave some polypeptides having defined secondary or tertiary structure, such as the native proteins indicated above; human $\alpha_1$-PI being the exception.

Based on the requirement that a denaturing environment is typically needed for periodontain to actively cleave a target polypeptide, periodontain has been classified as a cysteine proteinase. This observation is further confirmed by the fact that periodontain is readily inhibited by common cysteine proteinase inhibitors selected from the group consisting of dichloroisocoumarin, diisopropylfluorophosphate, leupeptin, tosyl-L-lysine chloromethyl ketone, Phe-Pro-Arg chloromethyl ketone, Z-Phe-Lys benzoyloxy methyl ketone, idoacetamide and L-trans-epoxysuccinyl-leucylamide-(4-guanidino)-butane (E-64). The ability of E-64 to inhibit periodontain further suggests that periodontain is more closely related to members of the papain family of enzymes than other cysteine proteinases of *P. gingivalis*.

The polypeptide of the present invention, preferably a cysteine proteinase, can be used as a source of inhibitors (in addition to those described above), such as inhibitory polypeptides and antibodies, for inhibiting the peptidase activity and thereby possibly reducing periodontitis, loss of tooth attachment and periodontal pocket formation. Antibodies to the cysteine proteinase of the invention can also be used to identify and/or isolate additional cysteine proteinases. Knowledge of specific cysteine proteinases can also be used to make inhibitory polypeptides against other cysteine proteinases. Such inhibitory polypeptides typically include from about 2 to about 20 amino acids from a polypeptide that the cysteine proteinase has at least some specificity for, such as the specificity that periodontain has for human $\alpha_1$-PI, further associated with a chemical group that inactivates the active site of the proteinase, such as chloromethyl ketone and organo-phosphinate compounds. These inhibitory polypeptides and antibodies may be employed to possibly reduce gingivitis, periodontitis, loss of tooth attachment, and/or periodontal pocket formation.

As described herein, an example of a specific cysteine proteinase is the cysteine proteinase periodontain isolated from *P. gingivalis* (SEQ ID NO: 1). Periodontain is a unique proteolytic enzyme, and the isolation and characterization of this novel bacterial proteinase will facilitate the development of therapies that function to inhibit the activity of this and other bacterial proteinases. Although not intending to be limiting, it is conceivable that periodontain is membrane anchored through a putative signal sequence which is not cleaved but remains as a membrane spanning domain similar to other members of the papain family of cysteine proteinases. Periodontain is most frequently associated with the membrane and outer membrane vesicles in strains 2561 (ATCC Accession No: 33277, Bethesda, Md.), W50 (ATCC Accession No: 53978, Bethesda, Md.), W12, and 381, despite the fact that it is soluble in strain HG66 (FIG. 3). This is also in agreement with the distribution of other *P. gingivalis* proteinases.

A preferred cysteine proteinase of the invention, is the mature polypeptide containing amino acid 148 to amino acid 843 of SEQ ID NO: 1. As shown in FIG. 1, it is thought that the catalytic domain of periodontain corresponds to the cysteine and histidine residues residing in the heavy chain of the mature polypeptide.

The invention therefore includes a polypeptide having similarity with the amino acid sequence of SEQ ID NO: 1. The two amino acid sequences (i.e., the amino acid sequence of the polypeptide and the sequence of SEQ ID NO: 1) are aligned such that the residues are aligned to maximize the number of amino acids that they have in common along the lengths of their sequences; gaps in either or both sequences are permitted in making the alignment in order to maximize the number of shared amino acids, although the amino acids in each sequence must nonetheless remain in their proper order. The percentage amino acid identity is the higher of the following two numbers: (a) the number of amino acids that the two sequences have in common within the alignment, divided by the number of amino acids in SEQ ID NO: 1, multiplied by 100: or (b) the number of amino acids that the two sequences have in common within the alignment, divided by the number of amino acids in the candidate polypeptide, multiplied by 100.

A polypeptide of the invention also can include an active analog or active fragment thereof of a polypeptide containing amino acid 1 to amino acid 843 of SEQ ID NO: 1. An active analog or active fragment preferably is characterized by the same amidolytic activity properties with respect to a target polypeptide as is the polypeptide shown in SEQ ID NO: 1.

An active analog of the invention includes a polypeptide having one or more amino acid substitutions that do not eliminate amidolytic activity for a target polypeptide. For example, an active analog of the invention is characterized by the ability to cleave any denatured polypeptide and nondenatured serpin polypeptide in the RSL region of the serpin polypeptide.

Substitutes for an amino acid in the polypeptides of the invention may be selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$.

Analogs, as used herein, also include modifications. Modified cysteine proteinases include a cysteine proteinase that is chemically and enzymatically derivatized at one or more constituent amino acid, including side chain modifications, backbone modifications, and N and C-terminal modifications including acetylation, hydroxylation, methylation, amidation, and the attachment of carbohydrate or lipid moieties, cofactors, and the like. Modified cysteine proteinases of the invention will retain amidolytic activity with regards to a target polypeptide. For example, a modified cysteine proteinase of the invention will hydrolyze the peptide bond in the RSL region of a human $\alpha_1$-PI polypeptide at glutamic acid and alanine, and the phenylalanine and leucine peptide bond as described above and as shown in SEQ ID NO: 1.

Fragments of a cysteine proteinase of the invention include a portion of a cysteine proteinase containing deletions or additions of one or more contiguous or noncontiguous amino acids such that the resulting polypeptide still retains amidolytic activity with respect to a target polypeptide. An example of an active fragment of a polypeptide of the invention is the catalytic domain of the heavy chain polypeptide containing amino acid 148 to amino acid 629 SEQ ID NO: 1.

The polypeptide of the invention can be obtained by several methods. Isolation of the polypeptide present on the surface of a cell producing the proteinase typically requires lysis of the cell followed by purification. Such purification methods are well known in the art and the following represent nonlimiting examples of suitable protein purification procedures: fractionation on immunoaffinity, ion-exchange, hydroxyapatite, Phenyl-Sepharose HP, MonoQ HR 5/5, or MonoP columns; ethanol precipitation; reverse phase HPLC; chromatography on silica or on an ion-exchange resin such as DEAE; chromatofocusing; SDS-PAGE; ammonium sulfate precipitation; gel filtration using, for example, Sephadex G-75. Preferably, isolation of the polypeptide from *P. gingivalis* is accomplished using the parameters set forth in Table 1(acetone precipitation, Sephadex G-150, Mono FPLC, and TSK gel filtration) or a combination of hydroxyapatite, Phenyl-Sepharose HP, MonoQ HR 5/5 and MonoP column chromatography steps as described herein.

A cysteine proteinase of the invention may also be isolated from organisms other than *P. gingivalis*. Other organisms can express a cysteine proteinase that is encoded by a coding region having similarity to the mature polypeptide coding region. A "coding region" is a linear form of nucleotides that encodes a polypeptide, usually via mRNA, when placed under the control of appropriate regulatory sequences. The boundaries of a coding region are generally determined by a translation start codon at its 5' end and a translation stop codon at its 3' end. "Regulatory region" refers to a nucleic acid fragment that regulates expression of a coding region to which a regulatory region is operably linked. Nonlimiting examples of regulatory regions include promoters, transcription initiation sites, translation start sites, translation stop sites, and terminators. "Operably linked" refers to a juxtaposition wherein the components so described are in a relationship permitting them to function in their intended manner. A regulatory element is "operably linked" to a coding region when it is joined in such a way that expression of the coding region is achieved under conditions compatible with the regulatory region.

Alternatively, other organisms can express a cysteine proteinase from a recombinant coding region encoding the proteinase. The identification of similar coding regions in other organisms can be accomplished as described herein. A cysteine proteinase can be isolated using purification methods that are well known in the art. Alternatively, the proteinase can be chemically synthesized using methods that are well known in the art including, for instance, solid phase synthesis. Examples of, for instance, coding and regulatory regions are described herein.

The expression of periodontain from *P. gingivalis* and subsequent cleavage of a specific substrate results in a free amino acid or a free leaving group, each of which can be assayed using techniques known to those of skill in the art. Other methods can be based on immunogenic properties of periodontain, for instance immunoassays and histochemistry, the detection of mRNA, and PCR related methods, all of which are known to one of skill in the art.

As described in the Examples, the amino acid sequence of the amino-terminal end of a heavy chain polypeptide was used to identify the nucleotide sequence of the periodontain coding region (SEQ ID NO: 2). The nucleotide sequence was present in a publically available database containing the nucleotide sequence of the partially finished *P. gingivals* W83 genome. The nucleotide sequence of the genome of this bacterium is currently being determined by the Institute for Genomic Research and is available at www.tigr.org. However, even though the nucleotides that encode the *P. gingivalis* cysteine proteinase are know, there has been no indication that the nucleotides were in fact transcribed and translated. The data obtained from the database only contained the nucleotide sequence of a genomic clone; there was no disclosure that the nucleotides did or did not contain an open reading frame. Moreover, there is little data known to the art regarding regulatory regions required for either the transcription or the translation of a nucleotide sequence in *P. gingivalis*.

Thus, a person of ordinary skill, having the nucleotide sequence of the genomic clone, would not be able to predict that the open reading frame encoding periodontain was transcribed or translated. Moreover, even if there was a suggestion that the open reading frame was both transcribed and translated, there is no suggestion that the polypeptide encoded by the open reading frame would have the novel activity of periodontain.

Accordingly, the present invention is directed to a nucleic acid fragment encoding a polypeptide, particularly a cysteine proteinase, active analog (including active modification) or active fragment thereof. The nucleic acid fragment can have a nucleotide sequence as shown in SEQ ID NO: 2. Alternatively, nucleic acid fragments of the invention include those whose complement hybridize to SEQ ID NO: 2 under standard hybridization conditions as described herein. During hybridization the entire nucleotide sequence of the complement can hybridize with SEQ ID NO: 2. Preferably, at least about 15 nucleotides of the complement hybridize with SEQ ID NO: 2, more preferably at least about 50 nucleotides, most preferably at least about 100 nucleotides.

Alternatively, the nucleic acid fragment can have a nucleotide sequence encoding a polypeptide having the amino acid sequence or a fragment thereof as shown in SEQ ID NO: 1. An example of the class of nucleotide sequences encoding such a polypeptide is SEQ ID NO: 2. This class of nucleotide sequences is large but finite, and the nucleotide sequence of each member of the class can be readily determined by one skilled in the art by reference to the standard genetic code.

The identification of similar coding regions in other organisms can be accomplished by screening individual wild-type microorganisms for the presence of nucleotide sequences that are similar to the coding region of periodontain, which is shown in SEQ ID NO: 2. Screening methods include, for instance, hybridization of a detectably labeled probe with a nucleic acid fragment.

Standard hybridizing conditions are a modification of the conditions used by Church et al., *Proc. Natl. Acad. Sci.,* (USA) 81:1991 (1984): 0.5 M phosphate buffer, pH 7.2.7% SDS, 10 mM EDTA, at 68° C., and three washes, each for 20 minutes in 2×SSC, 0.1% SDS, at 65° C. Preferably, a primer will hybridize to the nucleotide sequence set forth in SEQ ID NO: 2 under standard hybridizing conditions. Generally the primer does not have to be complementary to all the nucleotides of the nucleic acid fragment as long as there is hybridization under the above-stated conditions.

"Complement" and "complementary" refer to the ability of two single stranded nucleic acid fragments to base pair with each other, where an adenine on one nucleic acid fragment will base pair to a thymine on a second nucleic acid fragment and a cytosine on one nucleic acid fragment will base pair to a guanine on a second nucleic acid fragment. Two nucleic acid fragments are complementary to each other when a nucleotide sequence in one nucleic acid fragment can base pair with a nucleotide sequence in a second nucleic acid fragment. For instance, 5'-ATGC and 5'-GCAT are complementary. The term complement and complementary also encompasses two nucleic acid fragments where one nucleic acid fragment contains at least one nucleotide that will not base pair to at least one nucleotide present on a second nucleic acid fragment. For instance, the third nucleotide of each of the two nucleic acid fragments 5'-ATTGC and 51-GCTAT will not base pair, but these two nucleic acid fragments are complementary as defined herein. Typically two nucleic acid fragments are complementary if they hybridize under the standard conditions referred to herein.

Preferred oligonucleotide primers are nucleic acid fragments complementary to a coding region or another nucleotide sequence that encodes an isolated cysteine peptidase. For instance, a primer can contain a consecutive series of nucleotides complementary to a portion of the nucleotide sequence encoding the polypeptide or a fragment thereof of SEQ ID NO: 1. Preferably, an oligonucleotide primer is about 15 base pairs, more preferably about 17 base pairs in length. Preferred oligonucleotide primers are degenerative primers. Such degenerative primers can be prepared in accordance with any region of interest as set forth in SEQ ID NO: 2. Methods of detectably labeling an oligonucleotide primer are well known to the art.

The nucleic acid fragment that is identified by the prepared primer is further analyzed to determine if it encodes a polypeptide with amidolytic activity for a target polypeptide as defined herein. Another method for screening individual microorganisms for the presence of nucleotide sequences that are similar to the coding regions of the present invention is the polymerase chain reaction (PCR).

Individual wild-type microorganisms containing nucleic acid fragments encoding a polypeptide of the invention can also be identified using an antibody. Preferably the antibody is directed to the cysteine proteinase periodontain. The production of antibodies to a particular polypeptide is known to a person of skill in the art, and is further detailed herein.

The use of hybridization of an oligonucleotide primer to a coding region present in individual wild-type microorganisms can be used as a method to identify the nucleotides of the coding region identical or similar to a coding region present in SEQ ID NO: 2. Two nucleic acid sequences are "similar" if the two nucleic acid sequences can be aligned so that a percentage of corresponding residues are identical. The two nucleotide sequences (i.e., the nucleotide sequence of the coding region and the nucleotide sequence of the coding region of SEQ ID NO: 2) are aligned such that the nucleotides of the start and stop codons are in register, then further aligned to maximize the number of nucleotides that they have in common along the lengths of their sequences; gaps in either or both sequences are permitted in making the alignment in order to place the nucleotides of the start and stop codons in register and to maximize the number of shared nucleotides, although the nucleotides in each sequence must nonetheless remain in their proper order. The percentage nucleotide identity is the higher of the following two numbers: (a) the number of nucleotides that the two sequences have in common within the alignment, divided by the number of nucleotides in SEQ ID NO: 2, multiplied by 100; or (b) the number of nucleotides that the two sequences have in common within the alignment, divided by the number of nucleotides in the candidate coding region, multiplied by 100. Preferably, two nucleic acid sequences have at least about 50%, more preferably at least about 70%, and most preferably at least about 90% identity. The coding region can then be isolated and ligated into a vector as described below.

As mentioned above, a nucleic acid fragment of the invention can be inserted in a vector. Construction of vectors containing a nucleic acid fragment of the invention employs standard ligation techniques known in the art. See, e.g., Sambrook et al, *Molecular Cloning: A Laboratory Manual.*, Cold Spring Harbor Laboratory Press (1989) or Ausubel, R. M., ed. Current Protocols in *Molecular Biology* (1994). A vector can provide for further cloning (amplification of the nucleic acid fragment), i.e., a cloning vector, or for expression of the polypeptide encoded by the coding region, i.e., an expression vector. The term vector includes, but is not limited to, plasmid vectors, viral vectors, cosmid vectors, or artificial chromosome vectors. Typically, a vector is capable of replication in a bacterial host, for instance *E. coli*. Preferably the vector is a plasmid.

Selection of a vector depends upon a variety of desired characteristics in the resulting construct, such as a selection marker, vector replication rate, and the like. Suitable plasmids for expression in *E. coli*, for example, include pUC(X), pKK223-3, pKK233-2, pTrc99A, and pET-(X) wherein (X) denotes a vector family in which numerous constructs are available. PUC(X) vectors can be obtained from Pharmacia Biotech (Piscataway, N.H.) or Sigma Chemical Co. (St. Louis, Mo.). pKK223-3, pKK233-2 and pTrc99A can be obtained from Pharmacia Biotech. pET-(X) vectors can be obtained from Promega (Madison, Wis.), Stratagene (La Jolla, Calif.), and Novagen (Madison, Wis.). To facilitate replication inside a host cell, the vector preferably includes an origin of replication (known as an "ori") or replicon. For example, ColE1 and P15A replicons are commonly used in plasmids that are to be propagated in *E. coli*.

An expression vector optionally includes regulatory regions (e.g., promoters) operably linked to the coding region. The invention is not limited by the use of any particular promoter, and a wide variety are known. Promoters act as regulatory signals that bind RNA polymerase in a cell to initiate transcription of a downstream (3' direction) coding region. The promoter used in the invention can be a constitutive or an inducible promoter. It can be, but need not be, heterologous with respect to the host cell. Preferred promoters for bacterial transformation include lac, lacUV5, tac, arc, T7, SP6 and ara.

An expression vector can optionally include a Shine Dalgarno site (e.g., a ribosome binding site), and a start site (e.g., the codon ATG) to initiate translation of the transcribed message to produce the enzyme. It can also include a termination sequence to end translation. A termination sequence is typically a codon for which there exists no corresponding aminoacetyl-tRNA, thus ending polypeptide synthesis. The nucleic acid fragment used to transform the host cell can optionally further include a transcription termination sequence. The rrnB terminators, which is a stretch of DNA that contains two terminators, T1 and T2, is an often used terminator that is incorporated into bacterial expression systems (J. Brosius et al., *J. Mol. Biol.*, 148:107–127 (1981)).

The nucleic acid fragment used to transform the host cell optionally includes one or more marker sequences, which typically encode a polypeptide that inactivates or otherwise detects or is detected by a compound in the growth medium. For example, the inclusion of a marker sequence can render the transformed cell resistant to an antibiotic, or it can confer compound-specific metabolism on the transformed cell. Examples of a marker sequence are sequences that confer resistance to kanamycin, ampicillin, chloramphenicol, and tetracycline.

Antibodies can be produced to a polypeptide having the sequence of SEQ ID NO: 1 or a polypeptide having a percentage amino acid identity of SEQ ID NO: 1 as described herein. Alternatively, antibodies can be made to an antigenic analog or antigenic fragment of a polypeptide having the sequence or a fragment sequence thereof of SEQ ID NO: 1. An antigenic analog (including antigenic modifications), and antigenic fragment of a polypeptide derived from SEQ ID NO: 1 is one that generates an immune response in an animal (i.e., it does not eliminate peptide antigenicity in an animal). Analogs and fragments used in this context are as defined above with respect to active analogs and active fragments.

Accordingly, an aspect of the invention is an immunogenic composition comprising an isolated cysteine proteinase, or an antigenic analog or antigenic fragment thereof, preferably the cysteine proteinase periodontain. The cysteine proteinase of the invention preferably has amidolytic activity to cleave, i.e., hydrolyze, a peptide bond in a target polypeptide.

The immunogenic composition can further include excipients or diluents that are pharmaceutically acceptable as carriers and compatible with the immunogenic composition. The term "pharmaceutically acceptable carrier" refers to a carrier(s) that is "acceptable" in the sense of being compatible with the other ingredients of a composition and not deleterious to the recipient thereof. Suitable excipients are, for example, water, saline, dextrose, glycerol, ethanol, or the like, and combinations thereof. In addition, if desired, the immunogenic composition may contain minor amounts of auxiliary substances such as wetting or emulsifying agents, pH buffering agents, and/or adjuvants which enhance the effectiveness of the immune-stimulating composition.

The immunogenic composition can be used in a method for protecting an animal from a disease caused by *P. gingivalis*. This method includes administering the immunogenic composition and eliciting antibodies to a cysteine proteinase, antigenic analog, antigenic fragment, or antigenic modification. The diseases that can be treated in this manner include periodontal diseases, which includes gingivitis and periodontitis. Clinical hallmarks of periodontitis include lose of tooth attachment and periodontal pocket formation.

Alternatively and preferably, periodontal diseases can be treated by the use of inhibitors of a cysteine proteinase. An inhibitor of a cysteine proteinase, preferably periodontain, can be present in a composition that preferably contains a pharmaceutically acceptable carrier. For instance, inhibitors can be applied systemically, subgingivally (e.g., subgingival irrigation) and/or by controlled release delivery directly into the periodontal pocket using methods well known to the art (see, e.g., Kornman, K., *J. Periodontol.*, 64:782–791 (1993)). Preferably, an inhibitor is applied subgingivally or by controlled release delivery.

The cysteine proteinase, active analogs and active fragments thereof can be used in a method of reducing growth of bacteria in vitro or in vivo. Preferably, the bacteria is a periodontal pathogen, i.e, a bacterial pathogen that causes periodontal disease, more preferably the bacteria is *P. gingivalis*. The inability of asaccharolytic *P. gingivalis* to utilize free amino acids makes the bacterium entirely dependant on an external peptide supply. The action of the polypeptides of the invention may be required for bacterial growth, and inhibition of the polypeptides of the invention may inhibit the in vivo growth of organisms, including *P. gingivalis*.

The present invention also includes a method for identifying and isolating an inhibitor of a polypeptide of the invention. The method includes identifying an agent that inhibits the amidolytic activity of the polypeptide by incubating the polypeptide with the agent under conditions that promote amidolytic activity of the polypeptide and determining if the amidolytic activity of the polypeptide is reduced relative to the anidolytic activity of the polypeptide in the absence of the agent

EXAMPLES

Objects and advantages of this invention are further illustrated by the following examples, but the particular materials and amounts thereof recited in these examples, as well as other conditions and details, should not be construed to unduly limit this invention.

Example 1

Isolation and Characterization of a Proteinase Derived From *P. gingivalis*

Materials and Methods

Reagents

Diisopropyl fluorophosphate, leupeptin, and 3,4 dichloroisocoumarin were purchased from Calbiochem, La Jolla, Calif. All other reagents, unless otherwise indicated, were obtained from Sigma Chemical Company, St. Louis, Mo. All reagents were of at least analytical grade.

Bacteria Cultivation

The *P. gingivalis* (HG66) strain (Dr. Roland Arnold, University of North Carolina, Chapel Hill, N.C.) was used for the purification of periodontain. Cells were grown anaerobically in 5 liters (L) of broth containing 150 grams (g) of trypticase soy broth, 25 g yeast extract (both from Difco, Detroit, Mich.), 25 milligrams (mg) hemin, 2.5 g cysteine, 0.5 g dithiothreitol (DTr), and 5 mg of menadione (all from Sigma), at 37° C. for 24 hours (h) in an atmosphere of 85% $N_2$, 10% $CO_2$, and 5% $H_2$. The seed culture was used to inoculate 100 L of the same broth and the bacterium was then grown in a 130 L fermentor (W. B. Moore, Inc., Easton, Pa.) at the University of Georgia Fermentation Plant. Cells were grown for 24 hours until late stationary phase of bacterial growth ($OD_{660}$>2.0). Additional strains, 2561 (ATCC Accession No: 33277), W50 (ATCC Accession No: 53978) (both from ATCC, Bethesda, Md.), W12, and 381 (both from Dr. Caroline A. Genco, Boston University Medical School, Boston Mass.), were grown under the conditions described above in 1 L volumes.

Cellular Localization

Whole cell culture mixtures were fractionated to determine localization of periodontain. Initially, a low speed centrifugation (6,000×g, for 20 minutes at 4° C.) was used to pellet the cells, after which the supernatant was subjected to high speed ultracentrifugation (100,000×g, for 120 minutes at 4° C.) to separate vesicles from the supernatant which contained all soluble proteins. For quantitation of proteolytic activity all samples were brought to an equal volume by the addition of 50 millimolar (mM) Tris, pH 7.4.

$\alpha_1$-PI Inactivation Assays

Detection of the proteolytic activity of periodontain was determined by following periodontain's ability to specifically inactivate $\alpha_1$-PI, using $\alpha$-chymotrypsin as a target proteinase as described by Nelson et al., *Anal Biochem.*, 260:230–236 (1998). Briefly, native $\alpha_1$-PI (0.15 nanomoles (nmols)) was mixed with samples containing a putative inactivating activity in assay buffer (50 mM Tris, 10 mM cysteine, pH 7.8 and allowed to incubate at time intervals of 0, 30, 60, 90, 120, 240 minutes after which an equimolar amount of $\alpha$-chymotrypsin (0.15 mmols) was added to complex any remaining functional $\alpha_1$-PI. The chymotrypsin substrate, N-Suc-Ala-Ala-Pro-Phe- para-nitroanalide in dimethyl sulfoxide, was added and, after a 4 minute incubation at 25° C., the reaction was stopped by the addition of 50 µl glacial acetic acid. Endpoint absorbance at 405 mm was read in a Molecular Devices SpectraMax Plus spectrophotometer (Molecular Devices, Sunnyvale, Calif.) and the percentage of $\alpha_1$-PI remaining was calculated from controls (no $\alpha_1$-PI, 0.15 nM $\alpha$-chymotrypsin) versus (0.15 nM $\alpha_1$-PI, 0.15 nM $\alpha$-chymotrypsin) in the 4 minute reaction with N-Suc-Ala-Ala-Pro-Phe-para-nitroanalide.

Inactivation of $\alpha_1$-PI by periodontain was further determined by electrophoresis. Briefly, $\alpha_1$-PI (2 µM) was incubated with periodontain (2 nM) for 0, 15, 30, 45, and 60 minutes before the reaction was stopped by the addition of an SDS sample buffer. A control sample was preincubated with 100 µM of L-trans-epepoxysuccinyl-leucylamide-(4-guanidino)-butane (E64) for 5 minutes prior to 60 minutes incubation with $\alpha_1$-PI. The samples were electrophoresed on a 12% separating gel. Subsequently, samples were separated on a 16% peptide gel to isolate a 3 kD fragment produced by this cleavage. Referring to SEQ ID NO: 4 and FIGS. 4 and 6, both N-terminal amino acid sequence analysis and mass spectroscopy of the isolated fragment revealed that the major cleavage site was after the glutamic acid residue and a minor cleavage site was after the phenylalanine relative to the Methionine-Serine bond which forms the "bait" region of the reactive site loop (RSL) and is attacked by HNE at the (*) position Proteinase Purification Bacteria were harvested at stationary phase, and the cells were removed by continuous centrifugation (Sharples AS-16P rotor, Alfa Laval Separation Inc., Warminster, Pa.). The cell-free culture fluid was concentrated to 5 L in a Pellicon system (Millipore, Bedford, Mass.) using a 30 kD molecular weight (MW) cut-off membrane, and then precipitated with 7.5 L of acetone at −10° C. The protein pellet was redissolved in 20 mM Bis-Tris, 150 mM NaCl, 0.02% $NaN_3$, pH 6.8 (buffer A), supplemented with 1.5 mM 4,4'-dithiopyridine disulfide, and dialyzed overnight against the same buffer in a 10 kD MW cut-off membrane (Spectra-Por, Spectrum Corp., Laguna Hills, Calif.) with two additional changes of buffer A supplemented with 5 mM $CaCl_2$. The dialyzed fraction was clarified by centrifugation (40,000×g, for 30 minutes), concentrated by ultrafiltration (Amicon PM-I 10 membrane, Millipore, Bedford, Mass.) and applied in 20 ml fractions, each representing 5 L of starting supernatant, to a Sephadex G-150 column (5×105 centimeters (cm)) (Amersham-Pharmacia, Uppsala, Sweden) equilibrated with buffer A, at a flow rate of 30 millimeter/hour (ml/h). The activity was pooled, dialyzed against 50 mM Tris, pH 7.4 (buffer B), and further purified by ion exchange chromatography on a Mono-Q column (FPLC system, Amersham-Pharmacia, Uppsala, Sweden), with elution in a linear gradient of 0 mM to 500 mM NaCl in buffer B. Activity was concentrated and final purification obtained by separation on a TSK-GEL G3000SW (TosoHaas, Montgomeryville, Pa.) column using 50 mM Tris, 200 mM NaCl, pH 7.4.

Electrophoresis

Enzyme purification and visualization of the heavy and light chains were monitored by sodium dodecyl sulfate-polyacrylamide gel electrophoresis (SDS PAGE) on a 10% separating gel using the Tris-HCl/Tricine buffer system according to Schagger et al., *Anal. Biochem.*, 166:368–379 (1987)). A nondenaturing PAGE (Davis, Ann. N.Y. Acad. Sci., 2:404–427 (1964)) in a 4–20% gradient gel was used to show the native protein as a single band.

Molecular Mass Determination

The mass of the native enzyme was determined by gel filtration using a TSK-GEL G3000SW (TosoHaas, Montgomeryville, Pa.) calibrated with gel filtration standards (Bio-Rad, Richmond, Calif.). The mass of the separated heavy and light chains from SDS-PAGE were estimated by scanning the gel using the Eagle Eye II imaging system (Stratagene, La Jolla, Calif.) and calculating a linear regression of low molecular weight electrophoresis standards (Amersham-Pharmacia, Uppsala, Sweden) as reference. Accurate molecular mass measurements of the digestion products of a, —PT after enzymatic inactivation employed the use of matrix assisted laser desorption ionization (MALDI), with mass spectra acquired using a Vestec MALDI Linear Time-of-Flight Mass Spectrometer (Perspective Biosystems, Perkin-Elmer, Foster City, Calif.) at the Mass Spectroscopy Facility (University of Georgia, Athens, Ga.) according to the manufacturer's instructions.

Protein Sequence Analysis

For amino-terminal sequence analysis, proteins resolved by electrophoresis were electrotransferred onto a polyvinylidene difluoride (PVDF) membrane according to Matsudaira (Matsudaira, J. Biol. Chem. 22(21):10035–10038 (1987)). Sequence analysis was performed with an Applied Biosystems 4760A gas-phase sequencer at the Molecular Genetics Instrumentation Facility (University of Georgia, Athens, Ga.) operated according to the manufacturer's recommendations.

Inhibition Studies

For inhibition studies, periodontain was used at a concentration which was capable of completely inactivating 0.15 nmols of $\alpha_1$-PI in our standardized assay (Nelson et al., *Anal. Biochem.*, 2:230–236 (1998)) after one hour of incubation. Representatives of the various classes of proteinase inhibitors, at indicated concentrations, were preincubated with enzyme for 5 minutes prior to the addition of $\alpha_1$-PI. The cleavage of inhibitor (%) was normalized to a native inhibitor control in order to give the relative percent inactivation for each compound or protein tested against periodontain. The compound, L-trans-epoxysuccinyl-leucylamide-(4-guanidino)-butane (E64), which stoichiometrically inhibits cysteine proteinases of the papain family, was used to titrate periodontain. This allowed us to quantitate stock solutions of periodontain in terms of active enzyme, and make dilutions to desired concentrations for the degradation experiments described below.

Protein and Peptide Degradation by Periodontain

The degradation of proteins was followed by using either native lysozyme or reduced-carboxymethylated-maleylated lysozyme (lysozyme-RCM), RCM), (30 micromolar (µM)). Either protein was incubated with periodontain (30 nM) in a final volume of 20 microliter (µl) of assay buffer for 0 and 15 minutes, 1 hour and 24 hours. The reaction was stopped by addition of 20 µl of SDS sample buffer (4% SDS, 20% glycerol, 0.125 M Tris-HCl, pH 6.8), followed by boiling for 5 minutes, after which the entire sample was electrophoresed on a 12% gel and stained in 0.1% Comassie Brilliant Blue to visualize the protein bands.

To determine the cleavage sites within the reactive site loop (RSL) of α1-PI, inhibitor (20 µg) was incubated with 1 µg of periodontain for 4 hours, after which the sample was subjected to 16% SDS-PAGE to separate the approximately 3 kD fragment obtained by cleavage within the loop. The fragment was analyzed for both amino terminal sequence and molecular mass using an automated protein sequencer and mass spectroscopy, respectively, as described above.

For analysis of the fragments obtained through digestion of the insulin β-chain, periodontain (8 nM) was incubated with this peptide substrate (40 µM) in assay buffer in a final volume of 90 µl for desired time intervals. After stopping the reaction by the addition of 10 µl of 10 normal (N)HCL, samples were centrifuged (10,000×g, 2 minutes) and the entire supernatant (100 µl) was subjected to reverse-phase HPLC. Sample application to a Beckman Ultrasphere 5 µm ODS column (4.6×250 mm) (Beckman-Coulter Instruments. Fullerton, Calif.) equipped with an Ultrasphere 5 µm ODS guard-column (4.6×45 mm) (Beckman-Coulter Instruments. Fullerton, Calif.) was carried out in 0.1% TFA in water (solvent A) and separations were performed with a linear gradient of 0.08% TFA in 80% acetonitrile/water (solvent B) over 40 minutes at a flow rate of 1 ml/minute. The peptide elution was monitored at 215 mm.

Gelatin Zymograph

Zymography analysis on gelatin gels was performed on pure samples of periodontain in the presence of 5 mM cysteine, with or without 100 µM of E64 (samples were incubated with E-64 for about 5 minutes). After the addition of SDS sample buffer, the samples were subjected to electrophoreses at 4° C. on a 10% SDS-PAGE with gelatin (Difco, Detroit Mich.) (0.1 mg/ml) incorporated into the gel. Following electrophoresis, the gel was washed twice with 2.5% weight/volume (w/v) Triton X-100 to remove the SDS and then incubated in activation buffer (50 mM Tris, 20 mM cysteine, pH 7.4) at 37° C. for two hours. The zymograph was developed in 0.1% Amido Black, with clearing zones (negative staining) indicating proteolytic digestion of the incorporated gelatin. The gelatin zymograph indicated that the periodontain heavy chain (55 kD) 3 contained the catalytic active site.

Cloning of Gene Fragment Encoding N-Terminus of Periodontain

Based on the N-terminal sequence of the heavy chain (55 kD) of periodontain (SEQ ID NO: 1), a pair of degenerate oligonucleotide primers (5'-ACNGA(G/A)GGNGTNCCNGC-3') (SEQ ID NO: 7) and (5'-NCGCATNGG(G/A)TC(G/A)TT-3') (SEQ ID NO: 8) corresponding to amino acid residues (TEGPA) (SEQ ID NO: 9) and amino acid residues (NDPMR) (SEQ ID NO: 10), respectively, were designed. The DNA fragment coding for the N-terminus of periodontain was amplified by PCR using Pwo DNA Polymerase (Boehringer-Mannheim/HoffMan LaRoche Ltd., Basel, Switzerland), and 10 nanograms (ng) of W50 P. gingivalis DNA (purified by the Purgene kit, Gentra Systems Inc., Plymouth, Minn.). PCR was carried out with 500 ng of primers for 1 minute at 94° C., 1 minute at 65° C., and 20 seconds at 72° C. The expected product of 69 basepairs was purified from a 2% agarose gel with the Ultrafree MC Millipore Filter (Millipore, Bedford, Mass.), phosphorylated at the 5' end with polynucleotide kinase (PNK), and blunt end ligated into a SmaI digested pUC19 vector. The fragment coding for the N-terminus of periodontain was identified by sequence analysis.

Identification of the Periodontain Gene

A database containing the unfinished P. gingivalis W83 genome (available from the National Center for Biotechnology Information (NCBI), Unfinished Microbial Genomes at www.nchi.nlm.gov was searched for the presence of nucleotide sequences corresponding to the NH$_2$-terminal amino acid sequences of both chains of periodontain using the TBALSTN algorithm (Altschul et al., Nuclei Acid Res., 25:3389–3402 (1997)). The sequence of the clone: gn1 |TIGR |P. gingivalis_112, which contained the translated sequence for both chains of periodontain, was retrieved from The Institute for Genomic Research (TIGR) database (http:www.tigr.org). The gene encoding periodontain was identified using the NCBI open reading frame (ORF) finder program (also found at NCBI) and the amino acid sequence, obtained by conceptual translation of the entire ORF, was further used for homology screening performed with the NCBI BLAST search tool.

Results

Enzyme Purification

Previous experience in purifying enzymes from culture supernatants of P. gingivalis indicated that ice cold acetone precipitation as an initial step was successful in separating active proteinases from the bulk of peptides and proteins present in or released into the growth medium. Similarly, G-150 gel filtration as an early step was also utilized (Chen et al., J. Biol. Chem., 267(26):18896–18901 (1992); Pike et al., J. Biol. Chem., 26(1):406–411 (1994)), both to resolve proteins into rough molecular weight fractions and to remove the excess heme and phytoheme that coprecipitate during acetone treatment. Subsequent anion exchange chromatography (Mono Q) and gel filtration (TSK) allowed periodontain to be purified to near homogeneity. Our yield of 11% corresponded to over 1 mg of pure protein per each 5 L of starting culture fluid (Table I).

TABLE I

Purification of P. gingivalis Periodontain

| Fraction Step | Volume ml | Total Activity Units[a] | Total Protein mg | Specific Activity units/mg | Purification fold | Yield % |
|---|---|---|---|---|---|---|
| Culture Fluid | 15,000 | 11,000 | ~300,000 | .04 | 1.00 | 100 |
| Acetone Precipitation | 60 | 8,100 | 3,500 | 2.3 | 58 | 74 |
| Sephadex G-150 | 120 | 6,550 | 32.3 | 203 | 5,070 | 60 |
| Mono-Q, FPLC | 5 | 1,958 | 5.40 | 363 | 9,065 | 18 |
| Gel Filtration, TSK | 6 | 1,200 | 3.26 | 368 | 9,203 | 11 |

[a]Based on 1 unit = the activity necessary to completely inactivate 0.15 nmol of $\alpha_1$-PI in 60 minutes at 37° C. using the assay described above.

Physical Properties

TSK gel filtration of the pure enzyme yielded a single protein peak that eluted with a MW of approximately 75 kD, based on a linear regression data analysis from standards (data not shown). However, a 10% SDS-PAGE containing 1 µg of pure periodontain yielded two distinct bands at 55 kD) (heavy chain) and 20 kD (light chain), suggesting periodontain, as a native protein, is a heterodimer (data not shown). Testing a nondenaturing PAGE containing 1 µg pure periodontain and 5 µg of albumin, albumin formed dimers, and to a lesser extent, trimmers when subjected to electrophoresis. Conversely, periodontain, under nondenaturing conditions, did not yield any bands indicating a dimer or trimer (data not shown).

Amino terminal sequence analysis of each of these subunits yielded the sequences of TEGVPAEVHALMDNGH-FANDPMR (SEQ ID NO: 11) and DEWKKIGSVSVK (SEQ ID NO: 12) for the heavy (55 kD) and light (20 kD) chains, respectively. Analysis of the single protein species isolated from the nondenaturing PAGE, gave two new amino terminal sequences in equimolar quantities, which corresponded to those described above, confirming that periodontain is a heterodimer. It should also be noted that either heating of the sample and/or presence of SDS in the gel buffer was sufficient to separate the heavy and light chains on electrophoresis, suggesting that the native heterodimer was stabilized by ionic interactions rather than a disulfide bridge or covalent bonds. Isoelectric focusing yielded a pI of 5.3 for the native protein (data not shown) while gelatin zymography indicated that the 55 kD heavy chain contained the catalytic active site but the 20 kD light chain was devoid of enzymatic activity.

Stability

Periodontain activity was detected over a broad pH range of about 6.0 to about 9.0, with the optimum being between a pH of about 7.5 to about 8.0. The enzyme was stable at 37° C., overnight, and at 4° C. for several weeks, when stored in the absence of cysteine. The presence of reducing agent resulted in a 50% loss of activity at 37° C. overnight, presumably because of autodigestion. Heating to 60° C. caused complete loss of activity. Samples were routinely stored at −80° C. for several months with less than a 10% loss in activity.

Activation and Inhibition

Periodontain was completely inactive in the absence of reducing agents, whereas full activity was achieved with either free cysteine, β-mercaptoethanol, dithiothreitol (DTT), or dithiothreitol (DTE) at 0.1 mM concentration. Unlike the gingipains, which have higher activity in free cysteine, no single reducing agent was superior in activating periodontain. Furthermore, increasing concentrations of these reagents (up to 10 mM) did not cause any additional stimulation of periodontain activity. Finally, calcium ions ($Ca^{2+}$) did not have a stabilizing effect and glycyl-glycine did not stimulate activity, indicating additional differences between periodontain and the gingipains (data not shown). Based on its requirement for a reducing environment to become active, periodontain can be classified as a cysteine proteinase, and this is confirmed by the fact that it is readily inhibited by common cysteine proteinase inhibitors (Table II). The ability of E-64 to inhibit periodontain suggests that this enzyme is more closely related to members of the papain family than other cysteine proteinases of P. gingivalis which are either not inhibited (Kgp) or only weakly inhibited (Rgp's) by this compound.

TABLE II

Inhibition Profile of Periodontain

| Inhibitor | Class | Concentration | Percent Inhibition |
| --- | --- | --- | --- |
| EDTA | Metallo | 25 mM | 0 |
| Dichloroisocoumarin | Serine | 0.5 mM | 2 |
| Diisopropylfluorophosphate | Serine | 0.5 mM | 5 |
| Leupeptin | Serine/Cysteine | 50 μM | 88 |
| Tosyl-L-lysine chloromethyl ketone | Serine/Cysteine | 5 mM | 91 |
| Phe—Pro—Arg chloromethyl ketone | Serine/Cysteine | 10 μM | 96 |
| Z-Phe—Lys benzoyloxy methyl ketone | Cysteine | 10 μM | 99 |
| Idoacetamide | Cysteine | 5 mM | 100 |
| E-64 | Cysteine | 100 μM | 100 |

Enzyme Specificity

Periodontain was originally identified as a unique proteinase which was able to inactivate $\alpha_1$-PI through proteolytic cleavage. From the 3 kD size difference of cleaved versus native $\alpha_1$-PI noted on SDS-PAGE, it was speculated that periodontain caused hydrolysis within the exposed C-terminal reactive site loop (RSL) of this molecule. Sequencing of the peptide generated by incubation of $\alpha_1$-PI with periodontain indicated that cleavage took place after the glutamic acid (amino acid residue 354 of SEQ ID NO: 3), and after phenylalanine (amino acid residue 352 of SEQ ID NO: 3) of the human $\alpha_1$-PI. However, screening numerous synthetic pNA substrates with either Glu or Phe specificity in the analogous position yielded no detectable cleavage by periodontain. Indeed, even when the synthetic substrate Phe-Leu-Glu-pNA, which mimics amino acid residues 352, 353 and 354 of the RSL of human $\alpha_1$-PI (SEQ ID NO: 3) was employed, no hydrolysis was detected, indicating that a specific amino acid residue at the site of hydrolysis does not dictate the specificity of this enzyme.

Further investigated into the activity of periodontain on protein and peptide substrates was performed to further elucidate cleavage specificity. However, the insulin β-chain was hydrolyzed to such an extent that individual cleavages could not be mapped, even at low E:S molar ratios (1:5000). Rather, the HPLC analysis revealed no less than 10 peptides were generated from this thirty amino acid polypeptide within 15 minute and complete digestion occurred in 60 minutes (data not shown). Next, the activity of periodontain on native proteins was examined. However, the enzyme was unable to degrade azocasein, casein, lysozyme, collagen, fibrin, plasminogen, and fibrinogen (data not shown). In contrast, when lysozyme was reduced, carboxymethylated, and maleylated, complete digestion was noted in less than 10 minutes. These results, together with activity detected on the gelatin zymograph, indicate that periodontain cleaves denatured or easily accessible polypeptide chains, but it cannot cleave whole proteins with defined secondary or tertiary structure, $\alpha_1$-PI being the exception.

Structure of the Periodontain Gene

The region encoding the N-terminal sequence of the 55 kD catalytic subunit of periodontain was amplified by PCR using degenerate primers and P. gingivalis W50 DNA. The 69 basepair PCR product was cloned and sequenced. Using this structural information, the gene encoding periodontain was extracted from the unfinished microbial genome at NCBI and found to encode an 843 amino acid residue protein with a calculated molecular weight of 93,127 Da (FIG. 1). The predicted size of the translated protein is approximately 20 kD larger than that found experimentally by both gel filtration and SDS-PAGE. However, examination of the gene product revealed that proteolytic processing of the translated protein at Arg-147 and Lys-629 would yield a prepropeptide, a heavy chain containing the active site, and a light chain derived from the C-terminal part of the proprotein that corresponds exactly to the experimentally determined amino terminal sequences for these subunits (FIG. 2).

Thus, the native protein would have a predicted molecular weight of 76,727 Da, composed of a 52,981 Da catalytic heavy chain and a 23,764 Da C-terminal light chain, with a calculated pI of 5.18. This is in agreement with the experimental findings of a native protein of about 70 to about 80 kD by gel filtration, composed of a catalytic subunit of 55 kD and a noncatalytic subunit of 23 kD by SDS-PAGE, with a pI of 5.3. These data suggest a potential role in the processing of the pro-form of periodontain by both gingipains R and gingipain K, all of which are abundantly present in P gingivalis.

Distribution of Periodontain

Using the cloned 69 basepair catalytic amino terminal fragment as a probe, Southern blot analysis on the W50 strain revealed a single hybridizing band with each of the restriction enzyme digests (data not shown). Furthermore, an $\alpha_1$-PI inactivating activity was detected in all P. gingivalis strains tested. Interestingly, periodontain was most frequently associated with the membrane and outer membrane vesicles in strains 2561, W50, W12, and 381, despite the fact that it was soluble in strain HG66 (FIG. 3). This is also in agreement with the distribution of other P. gingivalis proteinases (Chen et al., J. Biol. Chem., 267(26):18896–18901 (1992); Pike et al., J. Biol. Chem., 269(1):406–411 (1994)).

Discussion

The multiple trypsin-like proteolytic activities have a significant contribution to the virulence of P. gingivalis, for both invasion and host defense evasion. In support of this concept, deletion of the two genes (rgpA and rgpB) encoding various forms of gingipains R, has been shown to attenuate in vitro virulence of the knockout strain (Nakayama et al., J. Biol. Chem., 270:(40):23619–23626 (1995)). In addition, the use of antibodies to gingipains R polypeptide chain derived fragments has shown in vo protection against *P. gingivalis* infection in a mouse model system (Genco et al., *Infect, Immun.*, 66(9):4108–4114 (1998)).

Despite the importance of these bacterial proteinases, the abundance of host derived metalloproteinases and serine proteinases, including active HNE, in the gingival crevicular fluid of individuals with severe periodontitis, is still by believed to be the primary factor responsible for much of the extracellular matrix destruction which occurs in this disease (Cox et al., *J. Periodont. Res.*, 24:353–361 (1989)). The concentration of HNE within the neutrophil is near 3.0 μM, and it is likely to be as high as 268 μM at sites of inflammation (Travis et al., *Am. J. Respir. Crit Care Med.*, 150:S143–S146 (1994)), such as those that occur during the development of another major connective tissue disease, pulmonary emphysema.

The regulating inhibitor of HNE is $\alpha_1$-PI, a plasma protein which forms a complex with this proteinase and is rapidly removed from the circulation and degraded (Mast et al., *J. Biol. Chem.*, 266(24):15810–15816 (1991)). The inhibitor, however, can itself be inactivated by either oxidation at its reactive site or by proteolytic cleavage by nontarget proteinases within the RSL region (Travis et al., *Annu. Rev. Biochem.*, 52:655–709 (1983)), and it is believed that both mechanisms occur during the development of emphysema. Certainly, the high levels of active HNE in the GCF, despite the presence of $\alpha_1$-PI, would suggest that parallel mechanisms for inhibitor inactivation may be also occurring in periodontal disease (Travis et al., *Annu. Rev. Biochem.*, 52:655–709 (1983)). In this respect, it has been reported that whole cells or culture supernatants from *P. gingivalis* are capable of proteolytically inactivating $\alpha_1$-PI (Grenier, *Microbiology* 142: 955–961 (1996); Carlsson et al., *Infect. Immun.*, 43(2):644-648 (1984)), although it is clear that this is not due to any of the gingipain —R or —K forms since the inhibitor contains no basic residues within its RSL (Potempa et al *J. Biol. Chem.*, 273(34):21648–21657 (1998)). Thus, another proteinase(s) must be involved in this process, and it is likely that periodontain serves this purpose.

Periodontain was purified from *P. gingivalis* culture fluids and was found to be a cysteine proteinase that is apparently produced as a heterodimer. This enzyme is similar to the other characterized cysteine proteinases from *P. gingivalis* in that, all are primarily secreted in strain HG66, yet present on membranes and vesicles in all other strains. Each has a signal peptide sequence, a long prepropeptide, a large catalytic domain, approximately 50 kD, and an additional C-terminal extension (about 20 kD to about 40 kD). In contrast, whereas the gingipains have a restrictive specificity, periodontain is characterized by an apparently nonspecific proteolysis of peptides or denatured proteins. Although the ability of this enzyme to hydrolyze $\alpha_1$-PI, a native protein, is contrary to our premise of its inability to cleave proteins with defined structure, this can be explained by the fact that the RSL is present in a flexible, extended conformation protruding above the protein core (Elliott et al., *J. Mol. Biol.* 27:419425 (1998)) and, as such, may mimic a denatured protein or peptide.

From analysis of the N-terminus of the catalytic subunit and subsequent cloning of this fragment, it was possible to elucidate the entire gene sequence from the partially completed genome sequence for *P. gingivalis* obtained from NCBI. Searching the database of known sequences has revealed that periodontain is homologous to both prtT, a putative cysteine proteinase from *P. gingivalis*, and streptopain (EC 3.4.22.10), a secreted cysteine proteinase from *Streptococcus pyogenes* (Table III and FIG. 1). The prtT gene, which has recently been cloned and sequenced (Otogoto et al., *Infect. Immun.*, 61(1):117–123 (1993); Madden et al., *Infect. Immun.*, 63(1):238–247 (1995)), is believed to encode a putative proteinase of a 96 kD to a 99 kD protein. It is not surprising that periodontain and prtT have highly homologous sequences, being from the same organism. Indeed, rgpA and rgpB are two completely separate genes that code for almost identical proteins with significantly overlapping specificity. However, until the gene product for prtT has been purified and characterized, functional similarities between prtT and periodontain cannot be assessed.

TABLE III

Homology of Periodontain with Streptopain and prtT
(Identity/Similarity)

| Domain | Streptopain | prtT |
| --- | --- | --- |
| Prepropeptide | 27/44 | 35/56 |
| Catalytic Subunit | 37/52 | 52/69 |
| C-terminal Subunit | N/A | 24/42 |
| Full Length Protein | N/A | 34/52 |

Periodontain and prtT, containing 843 and 840 amino acid residues, respectively, are more than twice the size of the streptopain (398 residues) (FIG. 1) The function of the light chain of periodontain is presently unknown; however, the C-terminal domain for the putative prtT gene product has recently been shown to be identical to the putative product for a hemin regulated gene, hemR (Karunakaran et al., *J. Bacteriol.*, 179(6):1898–1908 (1997)). Due to the high homology of the catalytic domains of all three genes, we believe that periodontain most likely should be classified with prtT and streptopain as an additional member of the C10 family of cysteine proteinases, as recently outlined in (Barret, Rawlings, and Woessner, (eds), *Handbook of Proteolytic Enzymes*, Academic Press, London (1998)).

Because *P. gingivalis* is an asacchrolytic organism, it must acquire both carbon and energy predominantly from proteinaceous sources. Recent evidence using radiolabeled substrates has shown that while this organism is very efficient at taking up dipeptides, it is incapable of transporting single amino acids (which may endogenously be present in GCF) across bacterial cell membranes (Dashper et al., *J. Dent, Res.*, 77(5):1133 (1998)). This is supported by the fact that despite a large body of research performed on extracellular endoproteinase from *P. gingivalis*, no aminoproteinase or carboxyproteinase have thus far been described.

It is thought that the gingipains, which only have a specificity for either Lys-X or Arg-X bonds, would be restricted in their ability to degrade large proteins to the size of dipeptides or tripeptides which could then be transported into the bacterium. Therefore, it is possible that a number of broadly specific proteinases and proteinase, including periodontain, may be physiologically important to *P. gingivalis*, not necessarily as virulence factors, but rather for nutrient acquisition. This may be accomplished by three pathways. First, since periodontain is the only peptidase in *P. gingivalis* so far described which possesses the ability to inactivate $\alpha_1$-PI, this maybe a mechanism for increasing the levels of HNE, a nonspecific host proteinase which might be utilized in protein degradation. Second, in combination with HNE, periodontain may augment the degradation of peptides produced by the actions of the gingipains. Third, there is evidence that *P. gingivalis* produces a prolyl dipeptidyl peptidase (Kiyama et al., *Bioch. Bioph. Acta,* 1396:3946

(1998)), a prolyl tripeptidyl peptidase, and an uncharacterized collagenase. This proteolytic milieu in the GCF could aid in the final production of peptides capable of being taken up by *P. gingivalis*.

The complete disclosures of the patents, patent documents, publications, ATCC deposits, and electronically available material (e.g., GenBank amino acid and nucleotide sequence submissions) etc., cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An isolated nucleic acid encoding a polypeptide which has amidolytic activity for cleavage of a nondenatured serpin at a reactive site loop region of the serpin,
wherein a complement of the nucleic acid hybridizes to SEQ ID NO: 2 under hybridization conditions of 0.5 M phosphate buffer, pH 7.2, 7% SDS, 10 mM EDTA, at 68° C., followed by three 20 minute washes in 2×SSC, 0.1% SDS, at 65° C.

2. The isolated nucleic acid of claim 1 wherein the polypeptide is isolated from *Porphyromonas gingivalis*.

3. An isolated nucleic acid encoding a polypeptide which has amidolytic activity for cleavage of a nondenatured serpin at a reactive site loop region of the serpin,
wherein the encoded polypeptide comprises an amino acid sequence comprising amino acid 148 to amino acid 843 of SEQ ID NO: 1.

4. An isolated nucleic acid encoding a polypeptide which has amidolytic activity for cleavage of a nondenatured serpin at a reactive site loop region of the serpin,
wherein the encoded polypeptide comprises an amino acid sequence comprising amino acid 148 to amino acid 629 of SEQ ID NO: 1.

5. An isolated nucleic acid encoding a polypeptide comprising SEQ ID NO: 1.

6. An isolated nucleic acid encoding a polypeptide consisting of SEQ ID NO:1.

7. An isolated nucleic acid fragment encoding a polypeptide which is isolated from *Porphyromonas gingivalis* and has amidolytic activity for cleavage of a nondenatured serpin at a reactive site loop region of the serpin, wherein the nucleic acid has a nucleotide sequence comprising SEQ ID NO: 2.

8. The isolated nucleic acid of claim 3 wherein the polypeptide is isolated from *Porphyromonas gingivalis*.

9. A vector comprising the nucleic acid of claim 1.

10. The vector of claim 9 wherein the vector is an expression vector or a cloning vector.

11. The vector of claim 9 wherein the vector is selected from the group consisting of plasmid vectors, viral vectors, cosmid vectors, and artificial chromosome vectors.

12. An isolated oral bacterial polypeptide which has amidolytic activity for cleavage of a nondenatured human $\alpha_1$-proteinase inhibitor at a reactive site loop region of the inhibitor,
wherein the isolated polypeptide is encoded by the nucleic acid of claim 1.

13. The isolated polypeptide of claim 12 wherein the polypeptide has amidolytic activity in a solution comprising about 1 mM to about 500 mM Tris, about 500 $\mu$M to about 100 mM cysteine maintained at a pH of about 7 to about 8.

14. The isolated polypeptide of claim 12 which is isolated from *Porphyromonas gingivalis*.

15. The isolated polypeptide of claim 12 which is a cysteine proteinase.

16. The isolated polypeptide of claim 12 which has a molecular weight of about 70 kD to about 80 kD as determined by gel filtration.

17. The isolated polypeptide of claim 12 which cleaves the reactive site loop region of the inhibitor represented by SEQ ID NO: 4 between glutamine and alanine.

18. The isolated polypeptide of claim 17 which cleaves the reactive site loop region of the inhibitor represented by SEQ ID NO: 4 between phenylalanine and leucine.

19. An isolated polypeptide encoded by the nucleic acid of claim 1,
wherein the polypeptide has amidolytic activity for cleavage of a nondenatured serpin at a reactive site loop region of the serpin.

20. An isolated polypeptide which is an oral bacterial cysteine proteinase and has amidolytic activity for cleavage of a nondenatured serpin at a reactive site loop region of the serpin,
wherein the isolated polypeptide is encoded by the nucleic acid of claim 1.

21. The isolated polypeptide of claim 20 wherein the polypeptide has amidolytic activity in a solution comprising about 50 mM Tris, about 20 mM cysteine maintained at a pH of about 7.4 at 37° C.

22. The isolated polypeptide of claim 20 which is isolated from *Porphyromonas gingivalis*.

23. The isolated polypeptide of claim 20, wherein the polypeptide further nonspecifically cleaves the serpin in a denaturing environment.

24. An isolated polypeptide comprising an amino acid sequence represented by amino acid 148 to amino acid 843 of SEQ ID NO: 1.

25. An isolated polypeptide comprising an amino acid sequence represented by amino acid 148 to amino acid 629 of SEQ ID NO: 1.

26. An isolated polypeptide comprising an amino acid sequence represented by SEQ ID NO: 1.

27. An immunogenic composition comprising a polypeptide which has amidolytic activity for cleavage of a nondenatured serpin at a reactive site loop region of a serpin that is capable of eliciting antibodies in an animal,
wherein the polypeptide is encoded by the nucleic acid of claim 1.

28. A method for identifying an inhibitor of a polypeptide which has amidolytic activity for cleavage of a nondenatured serpin at a reactive site loop region of a serpin comprising isolating an agent that inhibits the amidolytic activity of the polypeptide by incubating the polypeptide encoded by the nucleic acid of claim 1 with the agent under conditions that promote amidolytic activity of the polypeptide and determining if the amidolytic activity of the polypeptide is reduced relative to the amidolytic activity of the polypeptide in the absence of the agent, whereby the inhibitor is selected.

29. The method of claim 28 wherein the polypeptide is isolated from *Porphyromonas gingivalis*.

30. A method of inhibiting the amidolytic activity of a polypeptide comprising combining the polypeptide with an agent selected from the group consisting of dichloroisocoumarin, diisopropylfluorophosphate, leupeptin, tosyl-L-lysine chloromethyl ketone, Phe-Pro-Arg chloromethyl ketone, Z-Phe-Lys benzoyloxy methyl ketone, idoacetamide and L-trans-epoxysuccinyl-leucylamide-(4-guanidino)-butane (E-64),
wherein the polypeptide has amidolytic activity for cleavage of a nondenatured serpin at a reactive site loop region of the serpin, and
wherein the polypeptide is encoded by the nucleic acid of claim 1.

31. A method of inhibiting the amidolytic activity of a polypeptide comprising:
identifying an inhibitor that inhibits the amidolytic activity of the polypeptide by incubating the polypeptide encoded by the nucleic acid of claim 1 with the agent under conditions that promote amidolytic activity of the polypeptide and determining if the amidolytic activity of the polypeptide is reduced relative to the amidolytic activity of the polypeptide in the absence of the agent; and
combining the polypeptide with the agent, wherein the polypeptide has amidolytic activity for cleavage of a nondenatured serpin at a reactive site loop region of the serpin.

32. A kit for inhibiting the amidolytic activity of a polypeptide comprising:

an agent selected from the group consisting of dichloroisocoumarin, diisopropylfluorophosphate, leupeptin, tosyl-L-lysine chloromethyl ketone, Phe-Pro-Arg chloromethyl ketone, Z-Phe-Lys benzoyloxy methyl ketone, idoacetamide and L-trans-epoxysuccinyl-leucylamide-(4-guanidino)-butane (E-64); and instructions for combining the agent with a polypeptide, wherein the polypeptide has amidolytic activity for cleavage of a nondenatured serpin at a reactive site loop region of the serpin, and wherein the polypeptide is encoded by the nucleic acid of claim 1.

* * * * *

SEQUENCE LISTING

```
<160> NUMBER OF SEQ ID NOS: 6

<210> SEQ ID NO 1
<211> LENGTH: 843
<212> TYPE: PRT
<213> ORGANISM: Porphyromonas gingivalis

<400> SEQUENCE: 1

Met Lys Lys Ser Phe Leu Leu Ala Ile Val Met Leu Phe Gly Ile Ala
 1               5                  10                  15

Met Gln Gly His Ser Ala Pro Val Thr Lys Glu Arg Ala Leu Ser Leu
            20                  25                  30

Ala Arg Leu Ala Leu Arg Gln Val Ser Leu Arg Met Gly Gln Thr Ala
        35                  40                  45

Val Ser Asp Lys Ile Ser Ile Asp Tyr Val Tyr Arg Gln Gly Asp Ala
    50                  55                  60

Glu Arg Gly Ile Thr Ser Gln Glu Gly Ser Pro Ala Tyr Phe Tyr
 65                  70                  75                  80

Val Ala Asn Arg Gly Asn Asn Glu Gly Tyr Ala Leu Val Ala Ala Asp
                85                  90                  95

Asp Arg Ile Pro Thr Ile Leu Ala Tyr Ser Pro Ile Gly Arg Phe Asp
                100                 105                 110

Met Asp Ser Met Pro Asp Asn Leu Arg Met Trp Leu Gln Ile Tyr Asp
            115                 120                 125

Gln Glu Ile Gly Leu Ile Leu Ser Gly Lys Ala Gln Leu Asn Glu Glu
        130                 135                 140

Ile Leu Arg Thr Glu Gly Val Pro Ala Glu Val His Ala Leu Met Asp
145                 150                 155                 160

Asn Gly His Phe Ala Asn Asp Pro Met Arg Trp Asn Gln Gly Tyr Pro
                165                 170                 175

Trp Asn Asn Lys Glu Pro Leu Leu Pro Asn Gly Asn His Ala Tyr Thr
            180                 185                 190

Gly Cys Val Ala Thr Ala Ala Gln Ile Met Arg Tyr His Ser Trp
        195                 200                 205

Pro Leu Gln Gly Glu Gly Ser Phe Asp Tyr His Ala Gly Ser Leu Val
    210                 215                 220

Gly Asn Trp Ser Gly Thr Phe Gly Glu Met Tyr Asp Trp Ile Asn Met
225                 230                 235                 240

Pro Gly Asn Pro Asp Leu Asp Asn Leu Thr Gln Ser Gln Val Asp Ala
                245                 250                 255

Tyr Ala Thr Leu Met Arg Asp Val Ser Ala Ser Val Ser Met Ser Phe
                260                 265                 270

Tyr Glu Asn Gly Ser Gly Thr Tyr Ser Val Tyr Val Gly Ala Leu
            275                 280                 285

Arg Asn Asn Phe Arg Tyr Lys Arg Ser Leu Gln Leu His Val Arg Ala
```

-continued

```
            290                 295                 300
Leu Tyr Thr Ser Gln Glu Trp His Asp Met Ile Arg Gly Glu Leu Ala
305                 310                 315                 320

Ser Gly Arg Pro Val Tyr Ala Gly Asn Asn Gln Ser Ile Gly His
                325                 330                 335

Ala Phe Val Cys Asp Gly Tyr Ala Ser Asp Gly Thr Phe His Phe Asn
                340                 345                 350

Trp Gly Trp Gly Gly Val Ser Asn Gly Phe Tyr Lys Leu Thr Leu Leu
                355                 360                 365

Ser Pro Thr Ser Leu Gly Ile Gly Gly Glu Gly Ile Gly Phe Thr Ile
370                 375                 380

Tyr Gln Glu Ile Ile Thr Gly Ile Glu Pro Ala Lys Thr Pro Ala Glu
385                 390                 395                 400

Ala Gly Thr Asp Ala Leu Pro Ile Leu Ala Leu Lys Asp Ile Glu Ala
                405                 410                 415

Glu Tyr Lys Ser Glu Ser Gly Leu Asn Val Gly Tyr Ser Ile Tyr Asn
                420                 425                 430

Thr Gly Glu Glu Gln Ser Asn Leu Asp Leu Gly Tyr Arg Leu Asn Lys
                435                 440                 445

Ala Asp Gly Glu Val Ile Glu Val Lys Thr Ser Ser Ile Asn Ile Ser
450                 455                 460

Trp Tyr Gly Tyr Gly Glu His Pro Glu Ser Phe Ser Leu Ala Pro Asn
465                 470                 475                 480

Gln Leu Ser Gln Gly Ile Asn Thr Ile Thr Leu Leu Tyr Arg Arg Thr
                485                 490                 495

Gly Thr Glu Gln Trp Glu Pro Val Arg His Ala Gln Gly Gly Tyr Val
                500                 505                 510

Asn Ser Ile Lys Val Asn Thr Thr Asp Pro Asn Asn Val Val Val Thr
                515                 520                 525

Val Asp Asn Asn Glu Gly Lys Leu Ser Ile Val Pro Asn Ser Phe Val
530                 535                 540

Ala Asp Leu Asn Ser Tyr Glu His Ser Thr Ile Thr Val Gln Phe Asn
545                 550                 555                 560

Ser Asp Ser Pro Asp Glu Ile Arg Thr Pro Val Ala Phe Ala Leu Ser
                565                 570                 575

Thr Gly Ala Thr Ala Asp Asp Val Ile Ser Leu Gly Trp Val Met Ala
                580                 585                 590

Glu Val Pro Gly Gly Ser Ser Asn Tyr Pro Val Val Trp Ser Lys Asp
                595                 600                 605

Val Leu Thr Leu Ser Glu Gly Asp Tyr Thr Leu Trp Tyr Arg Phe Ser
                610                 615                 620

Ile Asn Asn Gln Lys Asp Glu Trp Lys Lys Ile Gly Ser Val Ser Val
625                 630                 635                 640

Lys Thr Pro Thr Glu Tyr Thr His Pro Leu Phe Glu Val Gly His Asn
                645                 650                 655

Gln Thr Ser Thr Tyr Thr Leu Asp Met Ala His Asn Arg Val Leu Pro
                660                 665                 670

Asp Phe Thr Leu Lys Asn Leu Gly Leu Pro Phe Asn Gly Glu Leu Val
                675                 680                 685

Val Val Phe Arg Gln Thr Gln Ser Ser Gly Ser Leu Trp Ala Ala
                690                 695                 700

Gln Glu Thr Val His Ile Lys Gln Gly Glu Thr Phe Val Tyr Lys Pro
705                 710                 715                 720
```

```
Val Val Glu Gly Pro Ile Pro Asp Gly Ser Tyr Arg Ala Thr Leu His
                725                 730                 735

Ala Phe Val Asn Gly Gln Gln Gln Leu Tyr Leu Lys Gly Lys Arg Asn
                740                 745                 750

Tyr Thr Val Lys Ile Val Asn Gly Thr Ala Val Glu Ala Ile Glu Ser
                755                 760                 765

Ser Glu Glu Ile Arg Val Phe Pro Asn Pro Ala Arg Asp Tyr Val Glu
                770                 775                 780

Ile Ser Ala Pro Cys Ile Pro Gln Glu Thr Ser Ile Ile Leu Phe Asp
785                 790                 795                 800

Leu Ser Gly Lys Ile Val Met Lys Asn Ser Leu Ser Ala Gly His Gly
                805                 810                 815

Arg Met Asp Val Ser Arg Leu Pro Asn Gly Ala Tyr Ile Leu Lys Val
                820                 825                 830

Asp Gly Tyr Thr Thr Lys Ile Asn Ile Val His
                835                 840
```

<210> SEQ ID NO 2
<211> LENGTH: 2532
<212> TYPE: DNA
<213> ORGANISM: Porphyromonas gingivalis

<400> SEQUENCE: 2

```
atgaaaaaaa gttttctttt agccatagta atgctctttg cattgccat gcagggacat      60
tctgctccgg ttacgaaaga gcgagctttg agtctggctc ggctggcttt cgacaggta    120
tccttgcgaa tgggacaaac agcagtatct gacaagattt ccatcgatta cgtttatcgg    180
caaggagatg ctgagagggg tatcacatca aagaggaag ctctcctgc atatttttat    240
gtagctaatc gtggaaataa tgagggctat gctcttgtag cagcagatga cagaataccg    300
acaatttttag cctattcacc cattggccgt ttcgacatgg acagtatgcc ggacaatctt    360
cgcatgtggc tacaaattta cgatcaggaa ataggcctga tactttccgg aaaagctcag    420
ctcaatgaag agatattacg taccgagggc gtaccggctg aagtacatgc tctgatggat    480
aacggtcatt ttgccaacga tcccatgcga tggaatcaag gttacccatg aacaataag    540
gaaccactgc ttcctaatgg caatcatgcc tataccggct gtgttgctac tgctgcagca    600
caaatcatgc gctaccatag ctggccgctt caaggtgaag gctctttcga ttatcatgca    660
ggttcattag ttggcaactg gtccggcaca tttggtgaaa tgtacgactg gatcaatatg    720
cccggaaatc ccgaccttga taatctgact caatctcaag tggatgccta cgccacactg    780
atgcgtgatg tgagtgcatc tgtttcgatg agttttttatg aaaatggaag tggtacgtac    840
agcgtttatg tagtaggagc cttgcgaaac aactttcgct acaagcgttc actgcagcta    900
catgtacgcg ccttatatac ctcacaggag tggcacgata tgatccgcgg ggaacttgcc    960
tccggaaggc cggtctatta tgcagggaat aaccagagca taggacatgc tttcgtttgc   1020
gatggttatg cttcggatgg tactttccat ttcaactggg gttgggggag tgtttccaac   1080
ggcttctaca aactaacact cctctcgccg acttcgttgg gtatcggagg tgagggaata   1140
ggttttacca tttatcaaga gatcatcacc ggtatcgaac cggctaagac tcccgctgaa   1200
gccggtacag atgccttgcc gatcttggca ctgaaagaca tagaagccga gtataaaagt   1260
gaatccggat tgaacgtagg gtattcgata tataatacag gtgaagagca atcaaatctt   1320
gacctcggat acagattgaa caaggctgac ggagaagtca tagaggtgaa aacttcatct   1380
```

```
atcaatatct cttggtacgg atacggagag catcccgaga gtttctcatt ggcacctaat    1440
cagttgtcac aaggaatcaa caccatcacc ctactttatc gtcgcacagg caccgaacag    1500
tgggagccgg tacggcatgc acagggagga tatgtcaata gcattaaagt aaatacgaca    1560
gacccgaaca atgtcgtagt cacggtagat aataacgaag gcaagctcag tatcgtcccc    1620
aacagctttg tcgcagatct gaattcttat gaacatagta cgattacagt acagttcaat    1680
agcgacagcc ctgatgagat ccgtacaccc gtagcctttg ctctatctac aggagctact    1740
gcggacgatg taatatcttt gggctgggta atggctgaag ttccgggcgg tagcagcaac    1800
tatccggtgg tttggtctaa agacgttctc actctctcgg aaggcgacta tacattgtgg    1860
tatagatttt ccatcaacaa ccaaaaggat gaatggaaaa agatcggaag cgtgtcagta    1920
aaaacaccga cagagtatac gcacccctta ttcgaagtgg gccataatca aacttctacc    1980
tatacgctgg atatggcaca acagagta ttgcccgact ttacactcaa aaatctcgga    2040
ttgcctttca atggtgagtt ggttgttgtt ttccgccaaa cacaatcctc atcgggtct    2100 ttatgggcag ctcaagaaac agtacatatc aagcaaggag aaactttcgt atataaacct    2160
gttgtcgaag gccctatacc tgatggatcc tatcgtgcga ccctccatgc attcgtaaac    2220
ggacaacaac agttgtacct caaggggaaa aggaactaca cggtgaagat cgtcaatggt    2280
acagcggtag aagcaataga atcgtcagaa gagatcagag tattccctaa tccggcacgc    2340
gattatgtgg aaatatcggc accttgcatt ccccaagaaa catctatcat tcttttcgat    2400
ctgtcaggca agattgtcat gaagaatagt ttatcagcgg ggcatggcag aatggatgtc    2460
agccgacttc ctaatggggc ctacatcctt aaggtggatg gatatacgac gaaaataaat    2520
atagtgcact aa                                                        2532

<210> SEQ ID NO 3
<211> LENGTH: 418
<212> TYPE: PRT
<213> ORGANISM: Homo sapiens

<400> SEQUENCE: 3

Met Pro Ser Ser Val Ser Trp Gly Ile Leu Leu Ala Gly Leu Cys
  1               5                  10                  15

Cys Leu Val Pro Val Ser Leu Ala Glu Asp Pro Gln Gly Asp Ala Ala
                 20                  25                  30

Gln Lys Thr Asp Thr Ser His His Asp Gln Asp His Pro Thr Phe Asn
             35                  40                  45

Lys Ile Thr Pro Asn Leu Ala Glu Phe Ala Phe Ser Leu Tyr Arg Gln
         50                  55                  60

Leu Ala His Gln Ser Asn Ser Thr Asn Ile Phe Phe Ser Pro Val Ser
     65                  70                  75                  80

Ile Ala Thr Ala Phe Ala Met Leu Ser Leu Gly Thr Lys Ala Asp Thr
                 85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
```

-continued

```
                165                 170                 175
Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
            195                 200                 205

Val Asn Tyr Ile Phe Phe Lys Gly Lys Trp Glu Arg Pro Phe Glu Val
            210                 215                 220

Lys Asp Thr Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
                260                 265                 270

Thr Ala Ile Phe Phe Leu Pro Asp Glu Gly Lys Leu Gln His Leu Glu
                275                 280                 285

Asn Glu Leu Thr His Asp Ile Ile Thr Lys Phe Leu Glu Asn Glu Asp
            290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
                340                 345                 350

Leu Ser Lys Ala Val His Lys Ala Val Leu Thr Ile Asp Glu Lys Gly
                355                 360                 365

Thr Glu Ala Ala Gly Ala Met Phe Leu Glu Ala Ile Pro Met Ser Ile
            370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 4
<211> LENGTH: 15
<212> TYPE: PRT
<213> ORGANISM: Homo sapiens

<400> SEQUENCE: 4

Gly Ala Met Phe Leu Glu Ala Ile Pro Met Ser Ile Pro Pro Glu
1               5                   10                  15

<210> SEQ ID NO 5
<211> LENGTH: 840
<212> TYPE: PRT
<213> ORGANISM: Porphyromonas gingivalis

<400> SEQUENCE: 5

Met Lys Arg Ile Phe Tyr Thr Leu Gly Leu Leu Leu Cys Leu Pro
1               5                   10                  15

Met Leu Gln Ala Gly Pro Val Thr Arg Ser Lys Ala Glu Gln Thr Ala
            20                  25                  30

Lys Asn Phe Phe Ala Lys Arg Gln Pro Thr Leu Ser Ser Ser Thr Ala
        35                  40                  45

Ser Leu Arg Met Asp Phe Val Tyr Lys Ala Ala Glu Arg Glu Glu Ala
    50                  55                  60
```

```
Leu Phe Val Phe Asn Arg Gly Glu Lys Asp Gly Phe Leu Leu Val
 65                  70                  75                  80

Ala Ala Asp Asp Arg Phe Pro Glu Val Ile Gly Tyr Ala Phe Lys Gly
                 85                  90                  95

His Phe Asp Ala Ala Arg Ile Pro Asp Asn Leu Arg Gly Trp Leu Lys
                100                 105                 110

Gly Tyr Glu Arg Glu Met Leu Ala Val Met Asp Gly Lys Ala Glu Pro
            115                 120                 125

Ile Asp Pro Ile Arg Glu Ala Lys Pro Thr Arg Asp Leu Pro Ser Ser
        130                 135                 140

Ile Ala Pro Ile Leu Glu Thr Gly Glu His Ala Ser Asp Pro Ile Leu
145                 150                 155                 160

Trp Asp Gln Gly Tyr Pro Phe Asn Thr Leu His Pro Leu Leu Pro Ser
                165                 170                 175

Gly Gln Gln Ala Tyr Thr Gly Cys Val Ala Thr Ala Met Gly Gln Ile
            180                 185                 190

Met Arg His Tyr Lys Trp Pro Glu Lys Ala Ser Gly Glu Tyr Asp Tyr
        195                 200                 205

Tyr Asp Asp Met Thr Gly Thr His Thr His Tyr Ser Gly Thr Phe Gly
    210                 215                 220

Glu Thr Tyr Asn Trp Ser Lys Met Pro Gly Asn Ile Ser Val Gly Ile
225                 230                 235                 240

Ser Pro Glu Glu Val Lys Ala Leu Ser Thr Phe Met Arg Asp Val Ser
                245                 250                 255

Phe Ser Val Asn Met Gln Phe Ala Asp Phe Gly Ser Gly Thr Phe Ser
            260                 265                 270

Ile Phe Val Glu Arg Ala Leu Arg Glu Thr Phe His Tyr Lys Lys Ser
        275                 280                 285

Leu Arg Tyr Ile His Arg Ser Leu Leu Pro Gly Lys Glu Trp Lys Asp
    290                 295                 300

Met Ile Arg Lys Glu Leu Ala Glu Asn Arg Pro Val Tyr Tyr Ala Gly
305                 310                 315                 320

Ala Asp Gly Ser Met Gly His Ala Phe Val Cys Asp Gly Tyr Glu Pro
                325                 330                 335

Asp Gly Thr Phe His Phe Asn Trp Gly Trp Gly Met Ser Asn Gly
            340                 345                 350

Asn Phe Tyr Leu Asn Leu Leu Asn Pro Gly Ser Leu Gly Thr Arg Ala
        355                 360                 365

Gly Asp Gly Gly Tyr Ser Thr Asp Gln Glu Val Val Ile Gly Ile Glu
    370                 375                 380

Pro Ala Ser Asn Glu Val Pro Gly Ile Val Pro Asp Pro Thr Ile Thr
385                 390                 395                 400

Leu Tyr Gly Leu Gln His Asn Met Ser Asp Glu Ala Leu Asp Leu Ser
                405                 410                 415

Val Lys Ile Lys Asn Tyr Ser Thr Tyr Ala Gly Asp Val Lys Leu Ala
            420                 425                 430

Tyr Arg Leu Thr Leu Pro Asn Gly Thr Glu Thr Thr Asn Pro Ala Val
        435                 440                 445

Thr Val Pro Ile Val Trp Glu Asp Ile Ile Gly Glu Ser Thr Gly Asn
    450                 455                 460

Ile Thr Ile Pro Cys Ser Gln Phe Ala Glu Gly Lys Asn Thr Ile Ser
465                 470                 475                 480
```

```
Ile Leu Tyr Arg Thr Asp Gly Met Ala Asp Trp Lys Glu Leu Lys His
                485                 490                 495

Ile Leu Met Gly Leu Val Asn Lys Ile Glu Val Thr Met Pro Ala Gly
            500                 505                 510

Asp Val Ala Tyr Ser Val Ala Asp Ala Arg Ile Val Leu Lys Asp Gly
            515                 520                 525

Ser Leu Ser His Asp Leu Lys Ala Tyr Ser Asp Cys Lys Leu Ser Ala
            530                 535                 540

Thr Val Tyr Asn Pro Gly Thr Glu Glu Phe Arg Ser Arg Val Thr Phe
545                 550                 555                 560

Ala Leu Arg Asn Thr Glu Gly Arg Leu Tyr Phe Leu Gly Arg His Leu
                565                 570                 575

Val Glu Leu His Pro Gly Asp Glu Asp Gly Glu Lys Val Ser Leu Thr
            580                 585                 590

Ile Thr Gly Leu Lys Ala Arg Ala Gly Gln Tyr Met Leu Val Cys Thr
            595                 600                 605

Gly Asp Met Glu Ser Leu Met Glu Asp Ala Ser Trp Ile Glu Leu Ala
            610                 615                 620

Ser Ile Glu Val Ala Glu His Thr Ser Thr His Ser Ser Leu Leu Val
625                 630                 635                 640

Ala Ser Asn Pro Gln Ile Asp Leu Leu Thr Val His Arg Ala Asn Pro
                645                 650                 655

Glu Thr Leu Pro Thr Phe Ser Ile Thr Asn Glu Gly Gly Ala Thr Phe
                660                 665                 670

Ser Gly Lys Ile Glu Ile Val Ala Ile Lys Ala Phe Ser Glu Thr Phe
            675                 680                 685

Phe Gln Ala Lys Glu Glu His Met Ser Leu Ala Gln Gly Glu Thr Lys
            690                 695                 700

Val Leu Ser Pro Glu Leu Thr Ala Asn Ser Ser Leu Tyr Thr Asn Ala
705                 710                 715                 720

Glu Leu Phe Pro Asp Gly Thr Tyr Tyr Ile Val Ile Arg Glu Gln Gly
                725                 730                 735

Phe Trp Asp Pro Ile Asp Leu Phe Gly Asp Tyr Tyr Tyr Arg Ile Arg
            740                 745                 750

Leu Ile Thr Asp Leu Ser Ser Ser Asp Ile Ala Gly Lys Asp Val Ser
            755                 760                 765

Thr Ile Val Leu Tyr Pro Asn Pro Ala His Asp Tyr Val His Val Ala
770                 775                 780

Ile Pro Pro Thr Tyr Ala Gly Ser Thr Leu Arg Leu Phe Asp Ile Gln
785                 790                 795                 800

Gly Arg Met Gln Leu Ser Thr Lys Ile Glu Ser Ala Asp Met Arg Leu
                805                 810                 815

Asp Val Glu Arg Leu Pro Lys Gly Thr Tyr Ile Val Val Glu Asp
            820                 825                 830

Met Val Gly Lys Leu Phe Ile Arg
            835                 840

<210> SEQ ID NO 6
<211> LENGTH: 398
<212> TYPE: PRT
<213> ORGANISM: Streptococcus pyogenes

<400> SEQUENCE: 6

Met Asn Lys Lys Lys Leu Gly Ile Arg Leu Leu Ser Leu Leu Ala Leu
 1               5                  10                  15
```

-continued

```
Gly Gly Phe Val Leu Ala Asn Pro Val Phe Ala Asp Gln Asn Phe Ala
             20                  25                  30

Arg Asn Glu Lys Glu Ala Lys Asp Ser Ala Ile Thr Phe Ile Gln Lys
         35                  40                  45

Ser Ala Ala Ile Lys Ala Gly Ala Arg Ser Ala Glu Asp Ile Lys Leu
     50                  55                  60

Asp Lys Val Asn Leu Gly Gly Glu Leu Ser Gly Ser Asn Met Tyr Val
 65                  70                  75                  80

Tyr Asn Ile Ser Thr Gly Gly Phe Val Ile Val Ser Gly Asp Lys Arg
                 85                  90                  95

Ser Pro Glu Ile Leu Gly Tyr Ser Thr Ser Gly Ser Phe Asp Ala Asn
             100                 105                 110

Gly Lys Glu Asn Ile Ala Ser Phe Met Glu Ser Tyr Val Glu Gln Ile
         115                 120                 125

Lys Glu Asn Lys Lys Leu Asp Thr Thr Tyr Ala Gly Thr Ala Glu Ile
 130                 135                 140

Lys Gln Pro Val Val Lys Ser Leu Leu Asp Ser Lys Gly Ile His Tyr
145                 150                 155                 160

Asn Gln Gly Asn Pro Tyr Asn Leu Leu Thr Pro Val Ile Glu Lys Val
             165                 170                 175

Lys Pro Gly Glu Gln Ser Phe Val Gly Gln His Ala Ala Thr Gly Cys
         180                 185                 190

Val Ala Thr Ala Thr Ala Gln Ile Met Lys Tyr His Asn Tyr Pro Asn
     195                 200                 205

Lys Gly Leu Lys Asp Tyr Thr Tyr Thr Leu Ser Ser Asn Asn Pro Tyr
 210                 215                 220

Phe Asn His Pro Lys Asn Leu Phe Ala Ala Ile Ser Thr Arg Gln Tyr
225                 230                 235                 240

Asn Trp Asn Asn Ile Leu Pro Thr Tyr Ser Gly Arg Glu Ser Asn Val
             245                 250                 255

Gln Lys Met Ala Ile Ser Glu Leu Met Ala Asp Val Gly Ile Ser Val
         260                 265                 270

Asp Met Asp Tyr Gly Pro Ser Ser Gly Ser Ala Gly Ser Ser Arg Val
     275                 280                 285

Gln Arg Ala Leu Lys Glu Asn Phe Gly Tyr Asn Gln Ser Val His Gln
 290                 295                 300

Ile Asn Arg Ser Asp Phe Ser Lys Gln Asp Trp Glu Ala Gln Ile Asp
305                 310                 315                 320

Lys Glu Leu Ser Gln Asn Gln Pro Val Tyr Tyr Gln Gly Val Gly Lys
             325                 330                 335

Val Gly Gly His Ala Phe Val Ile Asp Gly Ala Asp Gly Arg Asn Phe
         340                 345                 350

Tyr His Val Asn Trp Gly Trp Gly Val Ser Asp Gly Phe Phe Arg
     355                 360                 365

Leu Asp Ala Leu Asn Pro Ser Ala Leu Gly Thr Gly Gly Gly Ala Gly
 370                 375                 380

Gly Phe Asn Gly Tyr Gln Ser Ala Val Val Gly Ile Lys Pro
385                 390                 395
```